United States Patent
Frist, Jr.

(10) Patent No.: US 10,872,537 B1
(45) Date of Patent: Dec. 22, 2020

(54) SYSTEMS AND METHODS FOR HEALTH EDUCATION, CERTIFICATION, AND RECORDATION

(71) Applicant: HealthStream, Inc., Nashville, TN (US)

(72) Inventor: Robert Frist, Jr., Nashville, TN (US)

(73) Assignee: HealthStream, Inc., Nashville, TN (US)

( * ) Notice: Subject to any disclaimer, the term of this patent is extended or adjusted under 35 U.S.C. 154(b) by 0 days.

(21) Appl. No.: 16/721,700

(22) Filed: Dec. 19, 2019

Related U.S. Application Data

(63) Continuation-in-part of application No. 16/576,200, filed on Sep. 19, 2019, which is a continuation of application No. 16/576,116, filed on Sep. 19, 2019.

(51) Int. Cl.
| | |
|---|---|
| *G09B 5/12* | (2006.01) |
| *G09B 19/00* | (2006.01) |
| *G06Q 50/20* | (2012.01) |
| *G09B 23/28* | (2006.01) |

(52) U.S. Cl.
CPC ............ *G09B 5/12* (2013.01); *G06Q 50/205* (2013.01); *G09B 19/00* (2013.01); *G09B 23/288* (2013.01)

(58) Field of Classification Search
CPC ...... G09B 23/28; G09B 23/288; G09B 23/30; G09B 5/012; G06N 3/006
See application file for complete search history.

(56) References Cited

U.S. PATENT DOCUMENTS

| | | |
|---|---|---|
| 4,895,518 A | 1/1990 | Arnold et al. |
| 7,013,325 B1 * | 3/2006 | Vivian ................ G09B 5/00 434/322 |
| 7,731,500 B2 | 6/2010 | Feygin et al. |

(Continued)

OTHER PUBLICATIONS

Riccardo Miotto et al., "Deep Learning for Healthcare: Review, Opportunities and Challenges." Briefings of Bioinformatics, 19(6), 2018, 1236-1246 (Year: 2018).

(Continued)

*Primary Examiner* — Peter R Egloff
(74) *Attorney, Agent, or Firm* — Andre J. Bahou; Christopher T. McNeill; Waller Lansden Dortch & Davis LLP

(57) ABSTRACT

A computer-implemented healthcare education simulation method includes storing, in one or more non-transitory computer storage devices, a plurality of healthcare worker user data records; storing, in the one or more non-transitory computer storage devices, a plurality of healthcare scenario simulation data records; receiving, from a client device, a request for a healthcare scenario simulation; determining, at one or more servers, an identity of a healthcare worker user based on the request for the healthcare scenario simulation; selecting, from the plurality of healthcare worker user data records, a first healthcare worker user data record based on the identity of the healthcare worker user; generating, at the one or more servers, a customized healthcare scenario simulation based on the first healthcare user data record and at least a portion of the plurality of healthcare scenario simulation data records; and transmitting the customized healthcare scenario simulation to the client device.

20 Claims, 20 Drawing Sheets

(56) References Cited

U.S. PATENT DOCUMENTS

| | | | |
|---|---|---|---|
| 7,993,290 | B2 | 8/2011 | Lund et al. |
| 8,034,006 | B2 | 10/2011 | Celik-Butler et al. |
| 8,192,367 | B2 | 6/2012 | Myklebust et al. |
| 8,333,720 | B2 | 12/2012 | Nysaither |
| 8,394,040 | B2 | 3/2013 | Strand et al. |
| 8,465,292 | B2 | 6/2013 | Nysaether et al. |
| 8,594,996 | B2 | 11/2013 | Liang et al. |
| 8,827,708 | B2 | 9/2014 | Christiansen et al. |
| 8,939,922 | B2 | 1/2015 | Strand et al. |
| 9,886,873 | B2 | 2/2018 | Patrickson et al. |
| 10,438,487 | B2 | 10/2019 | Patrickson et al. |
| 10,438,497 | B2 | 10/2019 | Patrickson et al. |
| 2002/0127525 | A1* | 9/2002 | Arington ............... G09B 7/04 434/262 |
| 2003/0149759 | A1 | 8/2003 | Hetherington et al. |
| 2003/0158467 | A1 | 8/2003 | Liebert |
| 2005/0277096 | A1* | 12/2005 | Hendrickson ........ G09B 23/285 434/262 |
| 2006/0069326 | A1 | 3/2006 | Heath |
| 2007/0299473 | A1 | 12/2007 | Matos |
| 2008/0171311 | A1 | 7/2008 | Centen et al. |
| 2009/0035740 | A1 | 2/2009 | Reed et al. |
| 2009/0148821 | A1 | 6/2009 | Carkner et al. |
| 2010/0028846 | A1 | 2/2010 | Cohen et al. |
| 2011/0117878 | A1 | 5/2011 | Barash et al. |
| 2012/0301864 | A1 | 11/2012 | Bagchi et al. |
| 2012/0310103 | A1 | 12/2012 | Musiol et al. |
| 2013/0280685 | A1* | 10/2013 | Patrickson ............. G09B 23/30 434/262 |
| 2014/0062694 | A1 | 3/2014 | Miladin et al. |
| 2014/0272869 | A1 | 9/2014 | Hambleton et al. |
| 2014/0277228 | A1 | 9/2014 | Quan et al. |
| 2015/0154367 | A1 | 6/2015 | Shetty et al. |
| 2015/0242498 | A1 | 8/2015 | Davis |
| 2015/0363572 | A1 | 12/2015 | Myklebust et al. |
| 2016/0148114 | A1 | 5/2016 | Allen et al. |
| 2017/0061301 | A1 | 3/2017 | Glass et al. |
| 2017/0084163 | A1 | 3/2017 | Shen |
| 2017/0161439 | A1 | 6/2017 | Raduchel et al. |
| 2018/0113867 | A1 | 4/2018 | Erpenbach et al. |
| 2018/0144656 | A1 | 5/2018 | Mitros |
| 2018/0293802 | A1 | 10/2018 | Hendricks et al. |
| 2018/0342179 | A1 | 11/2018 | Barash et al. |
| 2019/0139631 | A1 | 5/2019 | Eshelman et al. |
| 2019/0340943 | A1 | 11/2019 | Jimenez et al. |
| 2020/0105405 | A1 | 4/2020 | Brandt |

OTHER PUBLICATIONS

Benjamin Schickel et al., "Deep EHR: A Survey of Recent Advances in Deep Learning Techniques for Electronic Health Records (EHR) Analysis," IEEE J Biomed Health Inform. Sep. 2018; 22(5): 1589-1604 (Year:2018).

Margaret Rouse, "What is IBM Watson Assistant? Definition from WhatIs.com," Jul. 2018, WhatIs.com, whatis.techtarget.com/definition/IBM-Watson-Assistant.

"Watson Assistant—IBM Cloud," Feb. 3, 2020, IBM.com, https://webarchive.org/web/20200203010741/https://www.ibm.com/cloud/watson-assistant/.

* cited by examiner

1600

```
┌─────────────────────────────────────────┐
│ Storing a plurality of healthcare worker user data │ ── 1602
│                records                   │
└─────────────────────────────────────────┘
                    ↓
┌─────────────────────────────────────────┐
│ Storing a plurality of healthcare scenario simulation data │ ── 1604
│                records                   │
└─────────────────────────────────────────┘
                    ↓
┌─────────────────────────────────────────┐
│ Receiving, from a client device, a request for a │ ── 1606
│        healthcare scenario simulation            │
└─────────────────────────────────────────┘
                    ↓
┌─────────────────────────────────────────┐
│ Determining an identity of a healthcare worker user │ ── 1608
│ based on the request for the healthcare scenario │
│                simulation                │
└─────────────────────────────────────────┘
                    ↓
┌─────────────────────────────────────────┐
│         Continued on FIG. 16B            │
└─────────────────────────────────────────┘
```

Continued from FIG. 16A

↓

Selecting, from the plurality of healthcare worker user data records, a first healthcare worker user data record — 1610

↓

Generating a customized healthcare scenario simulation — 1612

↓

Transmitting the customized healthcare scenario simulation to the client device — 1614

1700

Continued from FIG. 17A

↓

Generating a customized resuscitation scenario simulation — 1710

↓

Transmitting the customized resuscitation scenario simulation to the client device — 1712

FIG. 17B

SYSTEMS AND METHODS FOR HEALTH EDUCATION, CERTIFICATION, AND RECORDATION

CROSS-REFERENCES TO RELATED APPLICATIONS

This application is a continuation-in-part of U.S. patent application Ser. No. 16/576,200, filed on Sep. 19, 2019, entitled "Systems and Methods for Health Education, Certification, and Recordation," and which is pending, which is a continuation of U.S. patent application Ser. No. 16/576,116, filed on Sep. 19, 2019, entitled "Systems and Methods for Health Education, Certification, and Recordation," and which is pending, all of which are incorporated by reference in their entireties.

TECHNICAL FIELD

The present disclosure generally relates to healthcare, and more particularly, to systems and methods for health education, certification, and recordation.

BACKGROUND

Certain personnel that work at healthcare facilities are required to be certified in certain healthcare protocols, such as cardiopulmonary resuscitation (CPR). Conventionally, these people renew their certification by attending a certification class. These classes may last several hours, and the attendee may attend at regular intervals such as every two years. For busy healthcare workers, attending such a class takes time away from caring for patients. Furthermore, some healthcare worker may use the skills taught in these certification classes often. These healthcare workers may not need the same amount of in-class training or practice as other healthcare workers that do not use those skills as often.

Computer simulations can be used to train medical personnel. However, conventional simulations do not adapt to a user's experience, role, or other characteristics of the user. This results in computer simulations that are static and the same for all users, which may be less effective at training a user in a desired medical application.

Thus, what is needed is are systems and methods that allow healthcare workers to adjust training programs and training simulations that include more flexibility in meeting healthcare protocol certifications and simulating medical scenarios.

SUMMARY

The present disclosure generally relates to healthcare training systems and methods. More particularly, the present disclosure relates to a novel application of care-based and competency-based training systems and methods.

The present disclosure, in one embodiment, contemplates a method for health education, certification, and recordation. The method may include a computer-implemented cardiopulmonary resuscitation (CPR) certification method. The method may include obtaining, at a server, a user input from a user interface. The user input may define an interval for a desired CPR certification schedule. The method may include generating, at the server, a CPR certification program. Generating the CPR certification program may include generating at least two task groups. Each task group of the at least two task groups may include a healthcare certification task. The method may include administering, at the server, the CPR certification program. Administering the CPR certification program may include assigning, at the interval defined by the user input, one task group of the at least two task groups to a user enrolled in the CPR certification program, and receiving an indication that the enrolled user has completed the healthcare certification task of the assigned one task group.

Another aspect of the disclosure includes a computer-implemented method. The method may include obtaining, at a computing device, an input that defines an interval for assigning task groups to an enrolled user. The method may include obtaining, at the computing device, a selection of a plurality of healthcare certification tasks. The method may include generating, at the computing device, a plurality of task groups. A task group of the plurality of task groups may include a healthcare certification task of the plurality of healthcare certification tasks. The method may include generating, at the computing device, a certification program corresponding to a healthcare protocol and associating the plurality of task groups with the certification program. The method may include administering, at the computing device, the certification program. Administering the certification program may include, in response to the arrival of a first start date, assigning, via the computing device, the task group to the enrolled user enrolled in the certification program, and receiving, at the computing device, an indication that the enrolled user has completed the healthcare certification task of the task group.

Another aspect of the disclosure may include a computer-implemented method. The method may include obtaining, at a server, an input that defines an interval for assigning task groups to an enrolled user. The method may include obtaining, at the server, a selection of a plurality of healthcare certification tasks. The method may include generating, at the server, a plurality of task groups. A task group of the plurality of task groups may include a healthcare certification task of the plurality of healthcare certification tasks. The method may include generating a plurality of trigger events. A trigger event of the plurality of trigger events may include a condition and data linking a first task group of the plurality of task groups to a second task group of the plurality of task groups. The method may include generating, at the server, a certification program corresponding to a healthcare protocol. Generating the certification program may include associating the plurality of task groups with the certification program. The method may include administering, at the server, the certification program. Administering the certification program may include, in response to the arrival of a first start date, assigning the first task group to the enrolled user enrolled in the certification program, and may include, in response to fulfillment of the condition of the trigger event of the first task group, assigning the second task group to the enrolled user.

The present disclosure includes several benefits that overcome the problems of the prior art. For example, certification programs generated or administered by the systems and methods of the present disclosure include one or more configurations that tailor the certification program to the preferences of enrolled users. The various configurations of the certification program that can be tailored include an interval (sometimes called a "frequency") at which users participate in healthcare certification tasks, the type(s) of users enrolled in the certification program (e.g., the certification program can be tailored to emergency room doctors, hospital secretaries, or other roles), and other configurations. The benefits also include, for example, systems and methods that (1) record events that occur during an encounter with a patient, (2) provide a customized walkthrough of a healthcare protocol to a user based on the user's experience, knowledge, training, or other characteristics, and (3) allow a user's participating in an actual or simulated medical scenario to work toward or maintain certification in a healthcare protocol.

Furthermore, the present disclosure includes several benefits that overcome problems with computer-provided medical simulations. The present disclosure provides simulations that are automatically customized for each individual medical worker. The customization can be based on a user's experience, role, healthcare protocol, or other similar criteria. The customization can be based on data received from other users of medical simulations. The customized medical simulations allow computer-provided simulations to train more effectively and address the needs specific to the medical worker user.

It is understood that both the foregoing general description and the following detailed description are exemplary and exemplary only, and are not restrictive of the disclosure as claimed.

The systems and methods disclosed herein improve the functioning of computers. For example, the systems and methods disclosed provide automated creation of healthcare certification programs and automated application of events performed by healthcare workers that contribute to their completion of a certification program. The systems and methods disclosed allow computers to generate certification programs and healthcare protocol walkthroughs that are tailored to the specialties of a healthcare worker. The systems and methods disclosed allow computers to generate healthcare protocol walkthroughs tailored to the specific patient being cared for based on that patient's characteristics. The systems and methods disclosed herein include computer systems that use programmable operational characteristics to customize and tailor the certification programs and healthcare protocol walkthroughs without tradeoffs in processor performance or increased time spent configuring certification programs.

The systems and method overcome the shortcomings of previous attempts by allowing personnel to become and stay certified in healthcare protocols without having to sacrifice their time in long certification classes every few years. The systems and methods also allow healthcare workers to apply their skills to maintaining certification, which reduces the amount of time they spend away from patients. The systems and methods tailor certification programs for users based on the users' characteristics and allows the users to performing certifying activities at customized intervals.

The systems and methods disclosed herein further improve the functioning of computers. For example, the systems and methods disclosed provide automated creation of healthcare scenario simulations. The systems and methods customize the healthcare scenario simulations based on characteristics of a participating healthcare worker user such as the user's specialty, role, experience, or other characteristics. The systems and methods can customize the healthcare scenario simulations to train team leaders.

The systems and method overcome the shortcomings of previous attempts by automatically customizing healthcare scenario simulations instead of providing pre-made, static, and permanent simulations as are found in previous attempts. Furthermore, performance in these customized simulations contribute to certification in certification programs the user is enrolled in.

BRIEF DESCRIPTION OF THE DRAWINGS

The accompanying drawings, which are incorporated in and constitute a part of the specification, illustrate exemplary embodiments of the disclosure. Together with the description, they serve to explain the objects, advantages, and principles of the disclosure. In the drawings:

FIG. 16A is a flowchart diagram illustrating another exemplary embodiment of a method for health education, certification, and recordation.

DETAILED DESCRIPTION

Overview

Reference will now be made in detail to exemplary embodiments of the disclosure, some aspects of which are illustrated in the accompanying drawings.

The present disclosure is directed to systems and methods for health education, certification, and recordation. As discussed below, the systems and methods of the present disclosure may provide a system the capability to administer a certification program for a healthcare protocol (e.g., cardiopulmonary resuscitation (CPR) or basic life support (BLS)), healthcare procedure, or healthcare technique (hereinafter, each is referred to as a "healthcare protocol"). The certification program includes one or more configurations that may tailor the certification program to the preferences of enrolled users. The various configurations of the certification program that can be tailored include an interval at which users participate in healthcare certification tasks, the type(s) of users enrolled in the certification program, or other configurations. In some embodiments, a user of the systems and methods disclosed herein may include a healthcare worker, a non-healthcare worker, an administrator at a healthcare facility, or another type of user.

The present disclosure is also directed to systems and methods that, in some embodiments, provide functionality to record events that occur during an encounter with a patient. The systems and methods may provide a user with a healthcare protocol walkthrough to guide the user is performing the steps of a healthcare protocol. The present disclosure is also directed to systems and methods disclosed herein that provide a user the capability to work toward or maintain certification in a certain healthcare protocol in response to participating in a training scenario or an actual medical episode.

Figure 1:
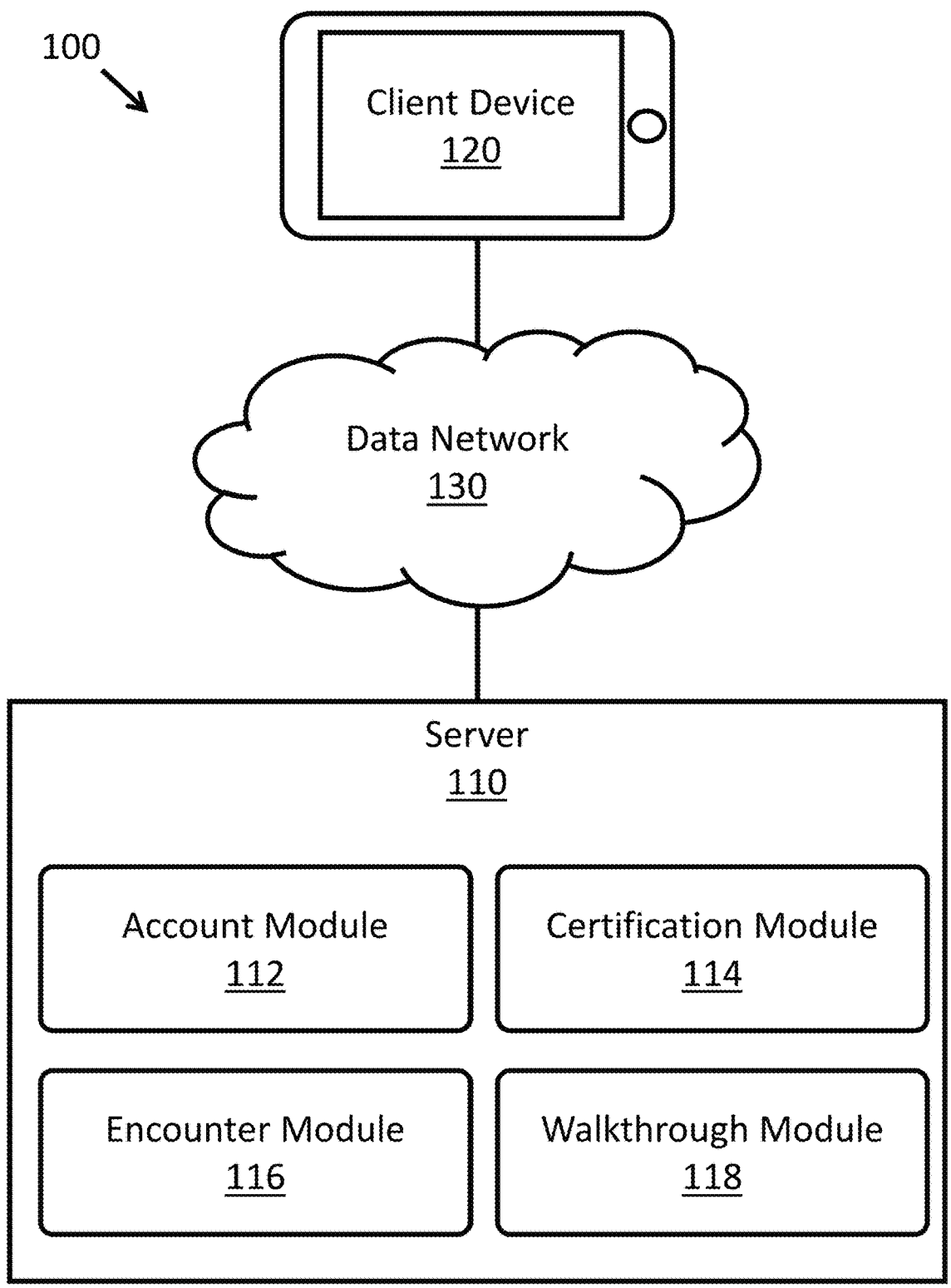
FIG. 1 is a schematic block diagram illustrating an exemplary system for health education, certification, and recordation.

FIG. 1 depicts one embodiment of a system 100. The system 100 may include a server 110. The server 110 may include modules. The modules may carry out functionality of the server 110. In one embodiment, the server 110 may include an account module 112. The account module 112 may store data associated with one or more users of the server 110 or one or more users of the modules of the server 110. The server 110 may include a module 114. The certification module 114 may administer one or more healthcare protocol certification programs. The server 110 may include an encounter module 116. The encounter module 116 generate an encounter record that may include data describing one or more events that occurred during a patient encounter. The server 110 may include a walkthrough module 118. The walkthrough module 118 may store one or more healthcare protocol walkthroughs. The walkthrough module 118 may customize a healthcare protocol walkthrough based on received data (e.g., a patient's age, sex, etc.) and may present the healthcare protocol walkthrough to a user. In some embodiments, the encounter module 116 may feed encounter data into the certification module 114, and the certification module 114 may determine whether an event recorded by the encounter data contributes, at least in part, to a user fulfilling a healthcare certification task of a certification program the user may be enrolled in.

In one embodiment, the system 100 may include a client device 120. The client device 120 may communicate with the server 110 via a data network 130 of the system 100. The client device 120 may send data to the server 110 or receive data from the server 110. The client device 120 may display the received data. The client device 120 may receive user input and send data to the server based on the user input. The user input may include input to configure the one or more modules 112, 114, 116, 118 of the server 110.

The following describes further details of one or more embodiments of the present disclosure. In some embodiments, the system 100 may include a server 110. The server 110 may include one or more computing devices. A computing device may include one or more processors, memory, one or more input/output (I/O) interfaces, or other computer components. The server 110 may include data storage. The data storage may include a file system, database, or other data-storing capabilities. The server 110 may include one or more modules. As used herein, the term "module" may refer to a software implementation, hardware implementation, or a combination of both. A module may include functionality that carries out steps, instructions, operations, or the like. A module may be implemented using program instructions, circuitry, or other implementation methods, as are described herein.

In some embodiments, the system 100 may include a client device 120. A client device 120 may include a personal computer, a tablet computer, a smartphone, or other computing device. The client device 120 may include software, such as a software application (app), that may perform functionality, such as communicating with the server 110. In some embodiments, some of the functionality of the one or more modules of the server 110 may be performed by the client device 120. The client device 120 may send data to the server 110 and may receive data from the server 110. The client device 120 may display various representations of data based on the data received from the server 110. The server 110 may be in data communication with the client device 120 over a data network 130 such as the Internet.

In some embodiments, the system 100 may include a data network 130. The data network 130 may allow the server 110, client device 120, and other devices to be in data communication. In one embodiment, the data network 130 may include a local area network (LAN), wide area network (WAN), the Internet, or other network. The data network 130 may include wired or wireless communication.

In one embodiment, the account module 112 may store, configure, or process data associated with one or more user accounts. A user account may store data associated with a user of the system 100. A user may include a person that works at a healthcare facility. A user account may store user personal information data. Personal information data may include the user's name, age, sex, or other personal data. The user account may store contact data. Contact data may include the user's address, phone number, email address, or other contract information. The user account may store occupational data. Occupational data may include one or more facilities the user works at, whether the user is a non-healthcare worker (e.g., an administrator, janitor, secretary, etc.) or a healthcare worker (e.g., a doctor, nurse, physician assistant, etc.), or one or more of the user's specialties (e.g., emergency medicine, neurology, oncology, etc.). The user account may store credential data. Credential data may include information related to the user's graduation from an educational institution (e.g., a graduation date, undergraduate institution, medical school, etc.) or licensing information (e.g., jurisdictions where the user is licensed, dates of obtaining a license, expiration date of a license, etc.). The user account may store certification information. Certification information may include information related to the user's certifications (e.g., a list of healthcare protocols the user is certified in, dates for which the user's certifications expire, etc.) The user account may store privilege information (e.g., admitting privileges, surgical privileges, prescribing privileges, etc.). The user account may store other information or data.

In one embodiment, the account module 112 may receive data related to the user of a user account. The account module 112 may update the user's account based on the received data. For example, as described below, in response to the account module 112 receiving an indication from the certification module 114 that the user has completed at least a portion of a certification program, the account module 112 may update the certification data of the user's account. In some embodiments, the account module 112 may output data stored in a user account. For example, the account module 112 may send user account data to the client device 120 to be viewed by a user.

In some embodiments, the account module 112 may store data only related to a user's certification in one or more healthcare protocols. Other data, such as electronic healthcare record (EHR) access rights, demographic data, or other data a healthcare computer system may track may be stored separately from the account module 112 or the server 110.

Certification Customization

In one embodiment, the server 110 may include the certification module 114. The certification module 114 may store one or more certification programs. A certification program may include a program administered to users in order to certify a user in a healthcare protocol. The certification module 114 may administer at least a portion of a certification program.

Figure 2A:
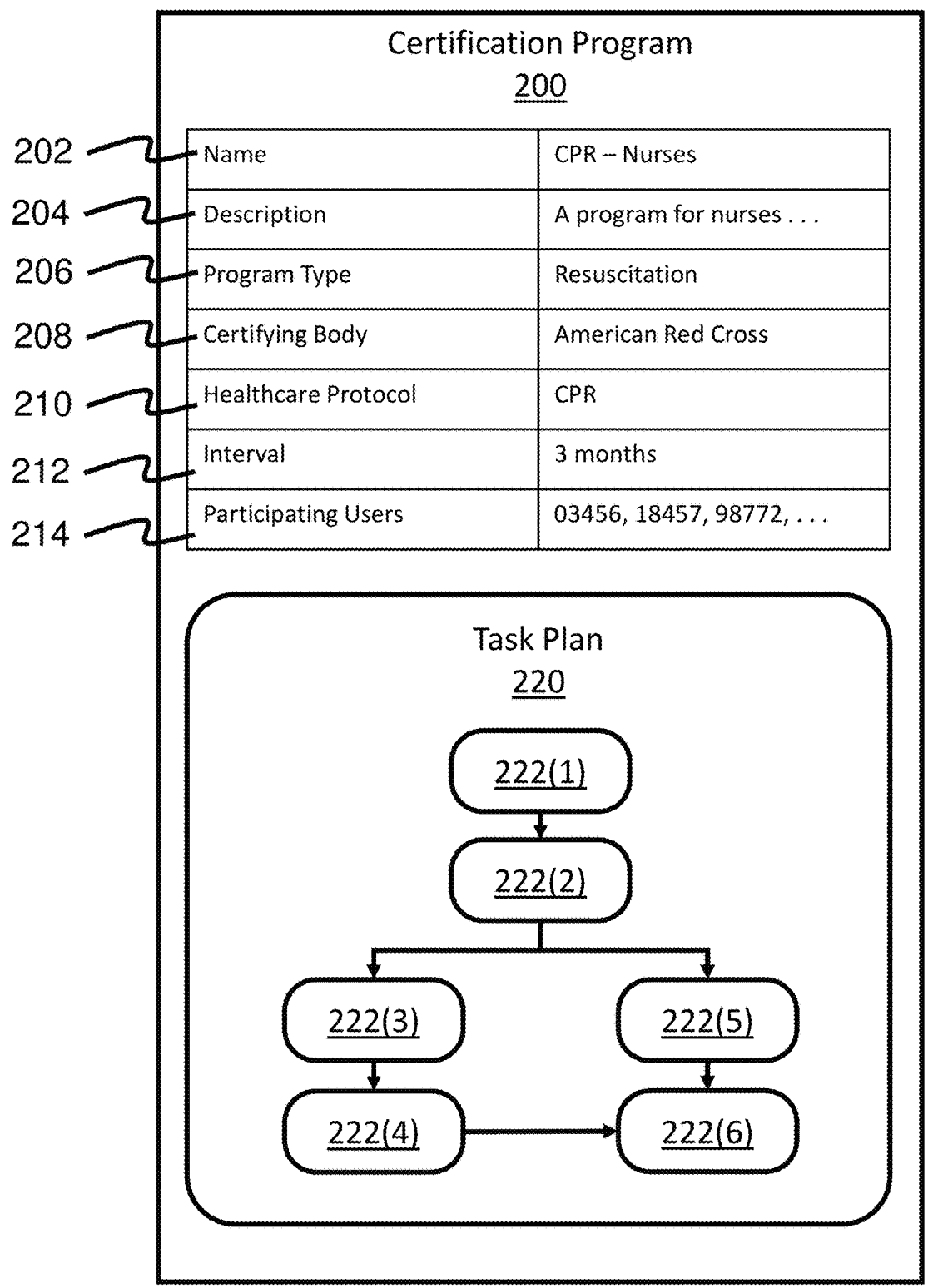
FIG. 2A is a block diagram illustrating an exemplary certification program for health education, certification, and recordation.

FIG. 2A depicts a data representation of one embodiment of a certification program 200. In some embodiments, the certification program 200 may include a name 202. The name 202 may briefly identify the certification program 200. The certification program 200 may include a description 204. The description 204 may briefly describe the certification program 200. In one embodiment, the certification program 200 may include a program type 206. The program type 206 may include a category to which one or more certification programs 200 may belong. The certification program 200 may include a certifying body 208. The certification program 200 may include a healthcare protocol 210. The healthcare protocol 210 may correspond to an actual healthcare protocol in which a participating user may be certified by participating in the certification program 200. The certification program 200 may include an interval 212. The interval 212 may indicate how often healthcare certification tasks, task groups, or other activities are assigned to a participating user. The certification program 200 may include one or more participating users 214. The one or more participating users 214 may include one or more users enrolled in the certification program 200. The certification program 200 may include a task plan 220. The task plan 220 may include one or more task groups 222(1)-(6). Each task group of the one or more task groups 222(1)-(6) may include healthcare certification tasks that a participating user may complete in order to become certified in the healthcare protocol 210 of the certification program 200. It should be noted that while the task plan 220 of FIG. 2A depicts six task groups 222(1)-(6), a task plan 220 is may include more or fewer task groups 222(1)-(n). Furthermore, the task plan 220 may include task groups 222(1)-(n) in a different order, with different paths through the task groups 222(1)-(n), or with other configurations.

In some embodiments, the name 202 of the certification program 200 may include a string of text. The name 202 may include a name configured by a user of the certification module 114. The name 202 may uniquely identify the certification program 200 among multiple certification programs 200 stored or administered by the certification module 114. An example of a name 202 may include "CPR—Nurses." In one embodiment, the description 204 may include text. The description 204 may further describe portions of the certification program 204. In some embodiments, the program type 206 may include a category of plans. A category of plans may include resuscitation, acute care, or another category. In some embodiments, a certification program 200 may include multiple program types 206. For example, a certification program for the healthcare protocol 210 of using an automated external defibrillator (AED) may include the program type 206 of resuscitation and acute care. In one embodiment, the certifying body 208 may include an organization or other entity that has the authority to certify persons in the healthcare protocol. Examples of a certifying body 208 may include the American Red Cross, the American Heart Association, or another organization.

In one embodiment, the healthcare protocol 210 may include cardiopulmonary resuscitation (CPR), a first aid procedure, AED, basic life support (BLS), advanced life support (ALS), or another healthcare protocol. The healthcare protocol 210 may correspond to an actual healthcare protocol that may include a series of steps a user should perform in a specified medical situation. For example, one or more steps a user should perform in response to encountering a person who is not breathing may include positioning the person on his/her back, checking for breathing, administering chest compressions, or blowing into the persons mouth.

In one embodiment, the interval 212 may include data related to how often a participating user of the one or more participating users 214 in the certification program 200 may be assigned a task group of the one or more task groups 222(1)-(6), healthcare certification task of one or more healthcare certification tasks 228(1)-(6), or other action related to the certification program 200. In one embodiment, the interval 212 may include three months, six months, twelve months, 24 months, or some other time interval. The previously mentioned intervals 212 may include once every three months, six months, twelve months, or 24 months. In some embodiments, the interval 212 may include intervals of equal time or may include intervals of different time lengths. In some embodiments, the interval 212 may be associated with a schedule for the certification program. In other embodiments, a participating user may be able to select an interval 212 that is convenient to the user's 214 schedule.

In one embodiment, a participating user may include a user with a user account administered by the account module 112. In one embodiment, the certification program 200 may include one or more user groups. The certification program 200 including a user group may allow one or more users with certain common characteristics to simultaneously participate in the same certification program 200. The certification module 114 may determine that users belong in the same user group based on user account data. In some embodiments, the certification module 114 may administer different certification programs 200 for the same healthcare protocol 210, but to different user groups.

In one embodiment, a user group may be based on one or more user characteristics. A characteristic may include a whether a user is a healthcare worker (e.g., doctor) or non-healthcare worker (e.g., secretary, lifeguard). A characteristic may include a specialty. For example, all neurosurgeons may belong to a first user group, and all intensive care unit (ICU) nurses may belong to a second user group. A characteristic may include other user characteristics.

In some embodiments, a certification program 200 may include one or more task groups 222(1)-(6). In response to a participating user of the one more participating users 214 completing certain task groups 222(1)-(6) of the certification program 200, the participating user may become certified in the associated healthcare protocol 210.

Figure 2B:
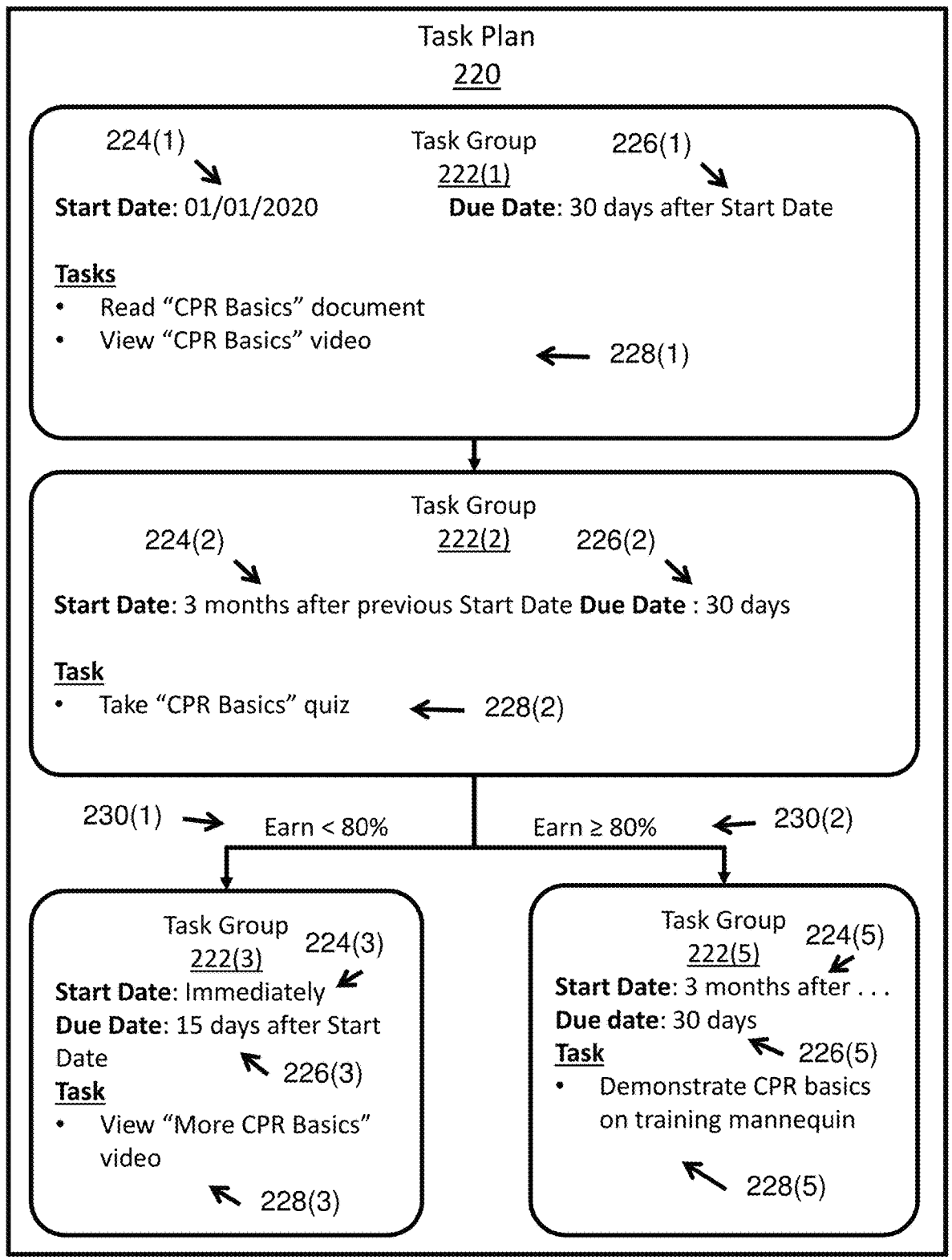
FIG. 2B is a block diagram illustrating a portion of an exemplary certification program for health education, certification, and recordation.

FIG. 2B depicts one embodiment of a portion of the task plan 220 portion of a certification program 200. The following describes the task group 222(1), although the description is also applicable to the other task groups 222(2)-(6). A task group 222(1) may include a start date 224(1). The start date 224(1) may include a date the task group 222(1) is assigned or available to a user. The task group 222(1) may include a due date 226(1). The due date 226(1) may include a date by which participating users 214 must complete the task group 222(1). The task group 222(1) may include one or more healthcare certification tasks 228(1). The one or more healthcare certification tasks 228(1) may include some action a user in the participating users 214 may perform to work toward completing the task group 222(1). In some embodiments, a task group 222(3) may include a trigger event 230(1). The trigger event 230(1) may include a condition under which a task group 222(3) is assigned to a user.

In one embodiment, the certification program 200 may include an order of the one or more task groups 222(1)-(6). The order of the one or more task groups 222(1)-(6) may include a chronological order in which at least a portion of the task groups 222(1)-(6) may be completed by a user. The order of the one or more task groups 222(1)-(6) may include branching paths. The certification program 200 may select a branch for a user based on a trigger event 230(1) or 230(2), a user characteristic, or some other data. In some embodiments, in response to a user completing the last task group 222(6) of a branch, the certification program 200 may assign the user to another task group 222(1)-(6) (e.g., the first task group 222(1) of the certification program 200).

As an example, FIG. 2B depicts a portion of one embodiment of the task plan 220 that includes multiple task groups 222(1)-(6). The task groups 222(1)-(6) may include a first task group 222(1). The first task group 222(1) may not include any preceding task groups. In response to a participating user of the one or more participating users 214 completing the one or more healthcare certification tasks 228(1) of the task group 222(1) and a start date 224(2) of the next task group 222(2) occurring, the participating user may be assigned the subsequent task group 222(2). After completion of the healthcare certification tasks 228(2) of the task group 222(2), the participating user 214 may be assigned either to a first branch with task group 222(3) or a second branch with task group 222(5). To which branch the participating user may be assigned may be based on the participating user's performance on a healthcare certification task 228(2), a characteristic of the participating user, or another factor.

In some embodiments, the start date 224(1) may include a date on which the task group 222(1) is assigned or available to a participating user of the one or more participating users 214. The task group 222(1) being assigned to the user may include the user being able to work on the one or more healthcare certification tasks 228(1) of the task group 222(1). The task group 222(1) being assigned to the user may include the user being able to view the task group 222(1) via the user's client device 120. In one embodiment, the start date 224(1) may include a day-month-year format, hour-minute-second format, or a combination of both.

In some embodiments, the due date 226(1) may include a date on which the task group 222(1) is due. The task group 222(1) being due may include that certain healthcare certification tasks 228(1) of the task group 222(1) must have been completed by the user on or before the due date 226(1). In certain embodiments, the due date 226(1) may be selected as any date that may be convenient for a participating user's schedule. In one embodiment, the due date 226(1) may include a day-month-year format, hour-minute-second format, or a combination of both.

In some embodiments, the one or more healthcare certification tasks 228(1) may include an action the user may complete to work toward certification in the certification program 200. Healthcare certification tasks 228(1) may include an educational task. An educational task may include attending an in-class lecture, viewing a slideshow presentation, viewing a video, listening to audio, reading a text, or receiving information in another way. In some embodiments, at least a portion of the educational task may be provided to the user via the client device 120. In one embodiment, a healthcare certification task 228(1) may include a practice task. A practice task may include the user practicing one or more healthcare techniques. A practice task may include a user practicing on a training mannequin (including a data-enabled training mannequin that may receive data from and send data to the server 110), taking a quiz, or performing some other action that helps the user practice what he or she may have learned from an educational task. A healthcare certification task 228(1) may include a demonstration task. A demonstration task may include the user demonstrating competency in the material presented during an educational task. A demonstration task may include the user demonstrating on a training mannequin, the user demonstrating to a training instructor, a multiple choice or free response test, or other demonstration techniques.

In one embodiment, the certification module 114 may receive data related to one or more healthcare certification task 228(1). The certification module 114 may determine from the received data whether the user completed the healthcare certification tasks 228(1). For example, the certification module 114 may receive data indicating whether a user viewed a video, whether a user properly performed on a training mannequin, or whether a user earned a certain score on a test. In one embodiment, a task group 222(1) may include multiple healthcare certification tasks 228(1). The task group 222(1) may be configured to allow a user to complete the healthcare certification tasks 228(1) of a task group 222(1) in any order or in a certain order specified by the task group 222(1). In some embodiments, in order to complete the task group 222(1), the user may complete all of the healthcare certification tasks 228(1) of the task group 222(1), a minimum number of healthcare certification tasks 228(1), or some other number or selection of healthcare certification tasks 228(1).

In some embodiments, a trigger event 230(1) of the task group 222(3) may include the arrival of a date or time. The trigger event 230(1) may include the completion of healthcare certification tasks 228(2) (e.g., viewing or reading educational material, earning a minimum score on a quiz, etc.), the completion of another task group 222(2), or another event.

In one embodiment, a start date 224(1) or a due date 226(1) may be relative to another date. For example, the due date 226(1) of a task group 222(1) may be 30 days after the start date 224(1). The start date 224(3) may be two weeks after the completion of a previous task group 222(2).

In some embodiments, the certification module 114 may administer multiple certification programs 200 for the same healthcare protocol 210. However, the multiple certification programs 200 may each include different frequencies 212, user groups, task groups 222(1)-(6), or orders of task groups 222(1)-(6). For example, the certification module 114 may administer a first CPR certification program 200 for emergency room doctors that may include a twelve-month interval 212 and a second CPR certification program 200 for nurses that may include a three-month interval 212. In some embodiments, a healthcare certification task of the one or more healthcare certification tasks 228(1)-(6) may be selected from a library of healthcare certification tasks stored by the certification module 114. The healthcare certification task library may be associated with the healthcare protocol 210 or certifying body 208 of the certification program 200.

In some embodiments, the selection of one element of the certification program 200 may influence the availability of other elements for the certification program 200. In response to a certification program 200 including a certain program type 206, the certification program 200 may be able to include only certain certifying bodies 208. In response to a certification program 200 including a certain certifying body 208, the certification program 200 may be able to include only certain healthcare protocols 210. For example, the American Red Cross may only certify CPR-related healthcare protocols. In response to selecting "American Red Cross" for the certifying body 208, a user may only be able to select "CPR" as a healthcare protocol 210 for the certification program 200. In one embodiment, the interval 212 may be influenced by the healthcare protocol 210, certifying body 208, or program type 206. In some embodiments, the healthcare protocol 210 may influence which task groups 222(1)-(6) or healthcare certification tasks 228(1)-(6) may be selected for a certification program 200. In some embodiments, a healthcare protocol 210 may be associated with a certifying body 204. For example, the American Red Cross may administer a first CPR certification and the American Heart Association may administer a second CPR certification.

In one embodiment, a user of the certification module 114 may configure a certification program 200. The user may configure one or more aspects of the certification program 200 such as the name 202, certifying body 204, healthcare protocol 206, or the interval 208. The user may select participating users 214. The user may configure other aspects of the certification program 200.

As an example, a certification administrator of a hospital system may access the certification module 114 through a client device 120. The certification administrator may use the certification module 114 to generate the certification program 200 of the FIG. 2A. In generating the certification program 200, the certification administrator may choose a name 202, description 204 program type 206, certifying body 208, healthcare protocol 210, and interval 212. The certification administrator may generate several task groups 222(1)-(6) in the certification program's 200 task plan 220. The certification administrator may configure trigger events 230(1)-(2), start dates 224(1)-(6), and due dates 226(1)-(6) for the task groups 222(1)-(6). The certification administrator may select healthcare certification tasks 228(1)-(6) from a healthcare certification task library for each task group 222(1)-(6). The certification administrator may add participating users 214 or user groups to the certification program 200.

In some embodiments, the certification module 114 may enforce that the one or more task groups 222(1)-(6), healthcare certification tasks 228(1)-(6) comply with the requirements of being certified in the selected healthcare protocol 210 for the certification program 200. If a certification administrator user uses the certification module 114 to generate a certification program 200, and the one or more task groups 222(1)-(6) or healthcare certification tasks 228(1)-(6) are insufficient to certify a user in the healthcare protocol 210, then the certification module 114 may notify the certification administrator (e.g., via an error message, pop-up message, or another type of message on a user interface) or may not allow the certification administrator to complete the certification program 200. As an example, referring the FIG. 2B, if the "CPR Basics" quiz of the healthcare certification task 228(2) is necessary for a participating user to complete in order to be certified in CPR, and the certification administrator does not include that healthcare certification task in one of the task groups 222(1)-(6), the certification module 114 may notify the certification administrator of the requirement and that the certification program 200, in its current configuration, does not include that requirement.

In some embodiments, the certification module 114 may determine whether one or more healthcare certification tasks 228(1)-(6) are completed in a correct order. A healthcare protocol 210 may include an order in which a portion of its tasks must be completed. In response to a certification administrator attempting to user the certification module 114 to generate a certification program 200 with one or more healthcare certification tasks 228(1)-(6) in an incorrect order, the certification module 114 may notify the certification administrator or may prevent the certification administrator from completing the configuration of the certification program 200. For example, as depicted in FIG. 2B, the task group 222(1) includes two healthcare certification tasks 228(1): read "CPR Basics" document and view "CPR Basics" video. The healthcare protocol 210 may allow a user to complete either task before the other. However, the healthcare protocol 210 may not allow a user to complete the healthcare certification task 228(2), take "CPR Basics" quiz, before the user has completed the healthcare certification tasks 228(1). If a certification administrator attempts to include the healthcare certification task 228(2) before the healthcare certification tasks 228(1), the certification module 114 may notify the certification administrator of the error.

In one embodiment, the certification module 114 may automatically generate at least a portion of a certification program 200. In some embodiments, the certification module 114 may automatically choose a name 202, description 204, program type 206, certifying body 208, healthcare protocol 210, or interval 212. The certification module 114 may automatically generate task groups 222(1)-(6) for the certification program 200. Automatically generating the task groups 222(1)-(6) may include configuring trigger events 230(1)-(2), start dates 224(1)-(6), due dates 226(1)-(6), and may include selecting healthcare certification tasks 228(1)-(6) for the task groups 222(1)-(6). The certification module 114 may automatically enroll participating users 214 or user groups. The certification module 114 may automatically enroll the participating users 214 or user groups based on characteristics of the participating users 214 or user groups.

In one embodiment, the certification module 114 may divide the one or more healthcare certification tasks 228(1)-

(6) for completing the certification program 200 based on the interval 212. For example, a CPR certification program 200 may include four hours of educational tasks, three hours of practice tasks, and one hour of demonstration tasks (for a total of eight hours of healthcare certification tasks 228 (1)-(6)). A user may configure the CPR certification program 200 with an interval 212 of six-month (i.e., four task groups 222(1)-(4) spread over during a two-year period). The one or more healthcare certification tasks 228(1)-(6) of a certification program 200 may be divided into task groups 222(1)-(6) in various ways. In one example, the certification module 114 may split the healthcare certification tasks 228(1)-(6) of the CPR certification program 200 into four two-hour certification occurrences, each certification occurrence including one or more of tasks. In one example, each two-hour task group 222(1)-(4) may include one hour of educational tasks, 45 minutes of practice tasks, and fifteen minutes of demonstration tasks. In another example, the first two task groups (1)-(2) may include the educational tasks, the third task group 222(3) may include the first hour of practice tasks, and the last task group 222(4) may include the last hour of practice tasks and the demonstration tasks. In some embodiments, the task groups 222(1)-(4) may each include tasks that may last different time lengths. For example, the first task group 222(1) may include three hours, the second task group 222(1) may include two hours, the third task group 222(3) may include three hours, and the last task group 222(4) may include one hour. The certification module 114 may divide the one or more healthcare certification tasks 228(1)-(6) based on other configurations, a sequence of the one or more healthcare certification tasks 228(1)-(6), or other factors.

In one embodiment, the certification module 114 automatically generating a certification program 200 may include the certification module 114 selecting healthcare certification tasks 228(1)-(6) based on a participating user's 214 characteristic. The certification module 114 may automatically generate a certification program 200 intended to be used by one or more participating users 214 with a certain characteristic. The characteristic may include the specialty of the participating user 214. For example, the certification module 114 may automatically generate a certification program 200 intended for emergency room doctors. Based on that configuration, the certification module 114 may select a set of healthcare certification tasks 228(1)-(6) configured for an emergency room doctor. In another embodiment, in response to the certification module 114 automatically generating a certification program 200 intended for participating users 214 that are non-healthcare workers (e.g., a janitor or lifeguard), the certification module 114 may select a set of healthcare certification tasks 228(1)-(6) that give more detail about the healthcare protocol 210 (because, for example, a janitor may not be as familiar with the healthcare protocol 210 as a healthcare worker).

In some embodiments, the certification module 114 may select one or more healthcare certification tasks 228(1)-(6) based on a location where the certification program 200 is intended to be used. For example, in response to the certification module 114 generating a certification program 200 intended to be used at a pediatric hospital, the certification module 114 may select one or more healthcare certification tasks 228(1)-(6) related to resuscitating children for a CPR certification program 200. For a certification program 200 intended for participating users 214 that work in a nursing home, the certification module 114 may select one or more healthcare certification tasks 228(1)-(6) related to resuscitating seniors for a CPR certification program 200. In one embodiment, the certification module 114 may perform some functionality, such as selecting the one or more participating users 214 or selecting the one or more healthcare certification tasks 228(1)-(6) based on output of an artificial intelligence (AI) engine.

In one embodiment, the certification module 114 may modify a certification program 200. A user may use the certification module 114 to modify a certification program 200, or the certification module 114 may automatically modify the certification program 200. Modifying the certification program 200 may include modifying the name 202, description 204, program type 206, etc. Modifying the certification program 200 may include modifying one or more task groups 222(1)-(6). Modifying a task group 222(1) may include adding or removing a healthcare certification task to/from the one or more healthcare certification tasks 228(1), adjusting a start date 224(1) or due date 226(1), adding or removing a trigger event, adding or removing one or more participating users 214 or user group, or may include other modifications.

In some embodiments, the certification module 114 may modify a certification program 200 based on data received by the server 100. The received data may mark a healthcare certification task 228(1)-(6) in a healthcare certification task library indicating that the healthcare certification task 228 (1)-(6) or a version of the healthcare certification task 228(1)-(6) should no longer be used. The received data may include a replacement healthcare certification task 228(1)-(6). The certification module 114 may modify a healthcare certification task 228(1)-(6) of a certification program 200 to no longer include a healthcare certification task 228(1)-(6) marked for replacement and to include a replacement healthcare certification task 228(1)-(6) or replacement version. For example, the certification module 114 may receive data indicating that an educational video is out-of-date. The certification module 114 may receive an up-to-date replacement video. The certification module 114 may remove a healthcare certification task 228(1)-(6) that includes the out-of-date video from the certification programs 200 and replace the removed healthcare certification tasks 228(1)-(6) with a new healthcare certification task 228(1)-(6) the include the up-to-date video.

In some embodiments, the library of healthcare certification tasks 228(1)-(6) may include healthcare certification tasks 228(1)-(6) provided by a patient safety organization (PSO). The server 110 may download the healthcare certification tasks 228(1)-(6) from the PSO, receive push updates, or otherwise receive the healthcare certification tasks 228(1)-(6) from the PSO. The PSO data may help the certification module 114 to operate data-enabled certification programs 200. In some embodiments, a data-enabled certification program 200 may allow participating users 214 to become certified in a healthcare protocol 206 based on up-to-date information endorsed by authorized governing bodies or other healthcare organizations. PSO data may include aggregated, de-identified data. The PSO data may be used for benchmarking.

In one embodiment, the certification module 114 may track a participating user's progress in adhering to a certification program 200. The certification module 114 may determine whether a participating user of the one or more participating users 214 has completed all healthcare certification tasks 228(1)-(6) or task groups 222(1)-(6) that have been due. In response to a participating user not being in compliance with a certification program 200 (e.g., the participating user has not completed all of the healthcare certification tasks 228(1) of a task group 222(1) by the due date 226(1) of the task group 222(1)), the certification module 114 may move the participating user to a remedial task group 222(1)-(6), modify the certification program 200 for the participating user to include one or more remedial task groups 222(1)-(6), or the certification module 114 may enroll the participating user in a remedial certification program 200. The certification module 114 may send a notification to an administering user in response to a participating user not being in compliance with a certification program 200. The administering user may determine what remedial steps should be taken regarding the participating user.

In one embodiment, in response to an enrolled user completing the certification program 200, the certification module 114 may issue a certification to the enrolled user. An enrolled user completing the certification program 200 may include the user completing all task groups 222(1)-(5) in the task plan 220 of the certification program 200. Completing the certification program 200 may include the user completing the last task group 222(6) of a branch in the task plan 220 of the certification program 200. Completing the certification program 200 may include completing a minimum number of task groups 222(1)-(6), a specified portion of the task groups 222(1)-(6), or some other subset of the task groups 222(1)-(6) of the task plan 220 of the certification program 200. The conditions required for completing a certification program 200 may be stored and maintained by the certification module 114.

In one embodiment, the certification module 114 may provide a user interface (e.g., via the client device 120) for managing one or more users, certification programs 200, or other certification functionality. The user interface may display a representation of a user. The representation may include the user's name, expiration date of a certification, or time until a certification expires. The user interface may display one or more participating users' 214 statuses regarding a certification program 200 the participating users 214 are enrolled it. The user interface may include one or more task groups 222(1)-(6) or healthcare certification tasks 228(1)-(6) the participating user has completed or not yet completed. The user interface may display other certification program data, such as a due date 226(1)-(6). In some embodiments, the certification module 114 may include a reminder configuration. The reminder configuration may indicate when to send a message to a user to remind him or her about one or more task groups 222(1)-(6) or healthcare certification tasks 228(1)-(6). The user interface may display a representation of a user group. The representation may include the group's name or identifier, one or more users pertaining to the group, characteristics of the user group (e.g., specialty, etc.) the configurations of a certification program 200 the group is enrolled in (e.g., interval 212, etc.), or other group information.

In some embodiments, data related to a user's certification in a healthcare protocol 210 may be stored in the certification module 114. In some embodiments, the data related to a user's certification may be stored by the account module 112, and the certification module 114 may send data to the account module 112 to update a user's account.

Encounter Records

In one embodiment, the server 110 may include an encounter module 116. The encounter module 116 may generate an encounter record. The encounter record may include data associated with a patient encounter. The encounter module 116 may track one or more events that occur during the patient encounter. The encounter module 116 may add the tracked events to the encounter record. Portions of the data of the encounter record may be used by other modules of the server 110.

Figure 3:
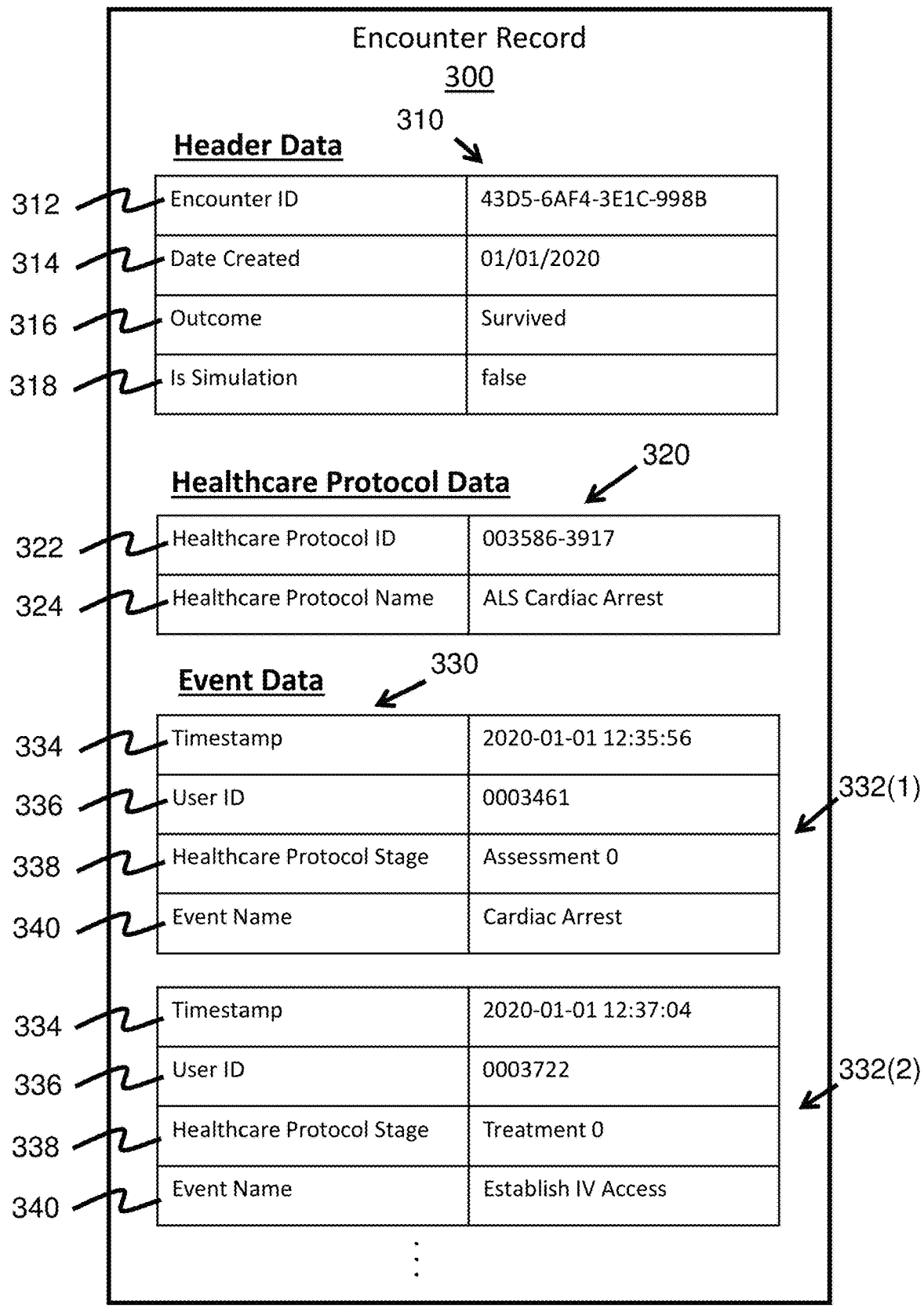
FIG. 3 is a block diagram illustrating an exemplary encounter record for health education, certification, and recordation.

FIG. 3 depicts one embodiment of an encounter record 300. The encounter record 300 may include header data 310. The header data 310 may include an encounter ID 302. The header data 310 may include a creation date 314. The header data 310 may include an outcome 316. The header data 310 may include a simulation indicator 318. In some embodiments, the encounter record 300 may include healthcare protocol data 320. The healthcare protocol data 320 may include a healthcare protocol ID 322. The healthcare protocol data 320 may include a healthcare protocol name 324. The encounter record 300 may include event data 330. The event data 330 may include one or more events 332. An event 332 may include a timestamp 334. An event 332 may include a user ID 336. An event 332 may include a healthcare protocol stage 338. An 332 event may include an event name 340.

In one embodiment, the encounter ID 312 may include a string of text. The encounter ID may uniquely identify the encounter record 300. The creation date 314 may include a timestamp of when the encounter record 300 was generated. The creation date 314 may include a time, a date, or other data. In some embodiments, the outcome 316 may include a string of text, a number, or other data. The outcome 316 may indicate an outcome of the event. Example outcomes may include that the patient survived, the patient was stabilized, the patient entered a comatose state, the patient died, or another outcome. In one embodiment, the simulation indicator 318 may include data to indicate whether the encounter associated with the encounter record 300 was a simulation or an actual medical encounter.

In some embodiments, the healthcare protocol ID 322 may include a string of text. The healthcare protocol ID 322 may uniquely identify the healthcare protocol used in the encounter. The healthcare protocol name 324 may include a string of text that includes the name of the healthcare protocol used.

In one embodiment, the timestamp 334 may include a timestamp of when the corresponding event 332 occurred. The timestamp may include a date, time, or other data. The user ID 336 may include data identifying user that performed the event 332, witnessed the event 332, or was otherwise involved in the event. In some embodiments, an event 332 may include multiple user IDs 336. The healthcare protocol stage 338 may include data identifying a stage of the healthcare protocol identified by the healthcare protocol ID 322. In some embodiments, a healthcare protocol may include one or more stages, and each stage may include one or more steps for a healthcare worker to perform. The healthcare protocol stage 338 may include the stage of the healthcare protocol that was occurring when the event 332 occurred. The event name 340 may include a string of text. The event name 340 may describe the event. The event name 340 may include "cardiac arrest," "established IV access," "check pulse," "patient stabilized," or another event name.

In some embodiments, an element of the encounter record 300 may be located in a different portion or section of the encounter record 300 than as described above or shown in FIG. 3. An encounter record 300 may include other elements than those described above.

In one embodiment, the encounter module 116 may generate at least a portion of an encounter record 300 during a patient encounter. The encounter module 116 may generate the encounter record 300 in response to a command or in response to receiving input data from a client device 120 of a healthcare worker participating in the patient encounter.

The encounter module 116 may automatically generate the encounter record 300 in response to detecting a medical event.

In some embodiments, the encounter module 116 may add an event 332 to an encounter record 300. The encounter module 116 may add the event 332 in response to a user creating the event 332 or may automatically create the event 332 and add the event 332 to the encounter record 300. In one example, after an encounter with a patient, a healthcare worker may use his or her client device 120 to input information related to the encounter to generate the event 332. In another example, the encounter module 116 may receive data from an EHR database related to patient encounter to generate the event 332. In yet another example, the encounter module 116 may receive data from a medical apparatus (e.g., an electrocardiograph machine) that indicates a certain event to generate the event 332.

In some embodiments, one or more portions of the encounter record 300 may include data in an Extensible Markup Language (XML) format, a JavaScript Object Notation (JSON) format, or other data format.

Adaptive Healthcare Protocol Walkthroughs

In one embodiment, the server 110 may include a walkthrough module 118. The walkthrough module 118 may include one or more healthcare protocol walkthroughs. A healthcare protocol walkthrough may include a series of steps a user may follow in order to perform a healthcare protocol. The walkthrough module 118 may display the series of steps to a user via the client device 120. The walkthrough module 118 may determine whether a user complies with at least a portion of the healthcare protocol. In some embodiments, the walkthrough module 118 may modify a healthcare protocol walkthrough based on received data, outcomes of a step of the walkthrough, or other data.

Figure 4:
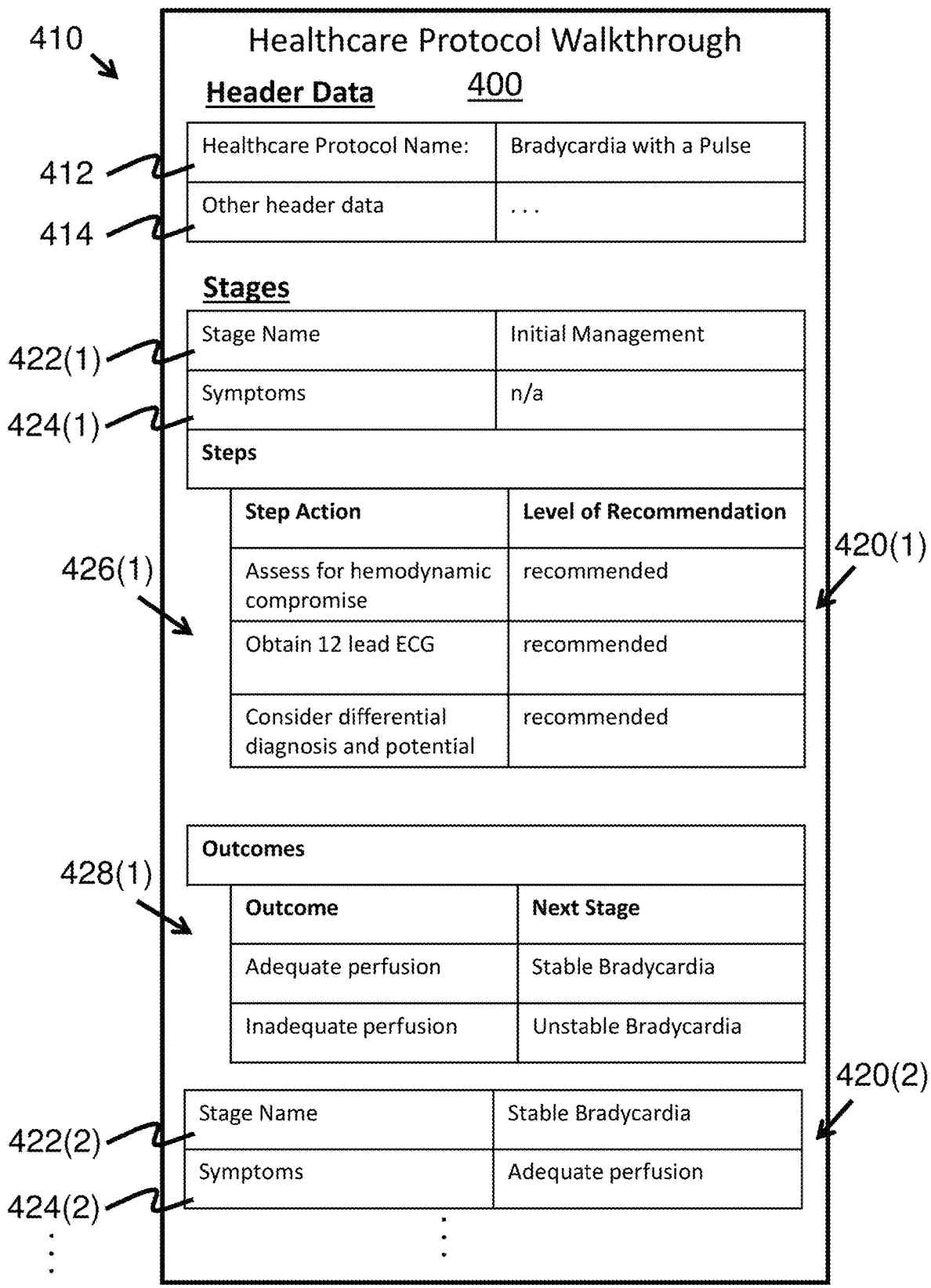
FIG. 4 is a block diagram illustrating an exemplary healthcare protocol walkthrough for health education, certification, and recordation.

FIG. 4 depicts one embodiment of a healthcare protocol walkthrough 400. The healthcare protocol walkthrough 400 may include data that may assist a healthcare worker in following a healthcare protocol. The healthcare protocol walkthrough 400 may include header data 410. The header data 410 may include a healthcare protocol name 412. The header data 410 may include other information about the healthcare protocol walkthrough 400. The healthcare protocol walkthrough 400 may include one or more stages 420. The one or more stages 420 may divide up the steps of a healthcare protocol into logical or conceptual groups. A stage 420 may include a name 422. A stage 420 may include one or more symptoms 424. A stage 420 may include one or more steps 426. A step 426 may correspond to an action that a user following the healthcare protocol may take. A step 426 may include a corresponding level of recommendation. A stage 420 may include one or more outcomes 428. An outcome 428 may include one or more conditions that may result from the steps 426 of the stage 420. An outcome 428 may include a corresponding next stage 420.

In one embodiment, the healthcare protocol name 412 may include a string of text that may identify the healthcare protocol. For example, as depicted in FIG. 4, the healthcare protocol name 412 of the healthcare protocol 400 includes "Bradycardia with a Pulse." In some embodiments, the stage name 422 may include a string of text that may identify the stage 420. For example, the stage 420(1) includes a name 422(1) that includes "Initial Management." The one or more symptoms 424 of a stage 420 may include a string of text or other data. The symptoms 424 may include one or more outcomes of a previous stage 420.

In some embodiments, the one or more steps 426 may include a string of text that indicates an action a healthcare worker may take. For example, the one or more steps 426(1) of the stage 420(1) include "Assess for hemodynamic compromise" and "Obtain 12 lead ECG."

In one embodiment, one or more steps 426 may include a level of recommendation corresponding to the step 426. A recommendation level may indicate the appropriateness of the step 426. The recommendation level of a step 426 may include a range from "required" to "prohibited." In one embodiment, a step 426 may include a recommendation level of "required." A "required" step 426 may include a step 426 that should always be performed. A recommendation level may include "recommended." A "recommended" step 426 may include a step 426 that is usually appropriate for the healthcare protocol, that is best-practice, that should almost always be done, or that are the standard of care for the healthcare protocol. A step 426 may include a recommendation level of "possible." A "possible" step 426 may include a step 426 that is sometimes appropriate. A "possible" step 426 may include a step 426 that is permissible based on factors such as patient presentation, care setting, resource availability, healthcare worker experience, or other factors. A step 426 may include a recommendation level of "not recommended." A "not recommended" step 426 may include a step 426 that is rarely appropriate, generally avoided, should not be performed under usual circumstances. A "not recommended" step 426 may include a step 426 that, based on patient presentation, is likely to offer no benefit or may even be potentially harmful. However, a "not recommended step" 426 may be appropriate in some limited situations. A recommendation level of "prohibited" may include a step 426 that should not be performed under any circumstances. In some embodiments, when a healthcare protocol walkthrough 400 is displayed to a user, each step 426 may indicate its level of recommendation (e.g., with a color, symbol, or other indicator).

As an examples of a healthcare protocol walkthrough 400 for a cardiac arrest response, a first step 424 may include "Defibrillate after rhythm recognition," and the first step 424 may include a "required" level of recommendation." A second step 424 may include "Administer Epinephrine every 3-5 minutes," the second step 424 may occur after the first step 424, and the second step 424 may include a recommendation level of "possible." A third step 424 may include "Administer Epinephrine," the third step 424 may occur before the first step, and the third step 424 may include the level of recommendation of "not recommended."

In some embodiments, in response to a first outcome 428 of a first stage 420(1), the healthcare protocol walkthrough 400 may continue on to a second stage 420(2), and in response to a second outcome of the one or more steps 424(1) of the first stage 420(1), the healthcare protocol walkthrough 400 may continue on to a third stage 420. For example, as depicted in FIG. 4, after a healthcare worker performs the steps 426(1) of the initial management stage 420(1), the patient may experience stable bradycardia. In response, the outcomes 428 may lead to the stable bradycardia stage 420(2). In response to the patient experience unstable bradycardia, the path 426 may lead to the unstable bradycardia stage 420 (not depicted in FIG. 4). In some embodiments, in response to a stage 420 including multiple possible outcomes 428, a healthcare protocol walkthrough 400 may branch to different stages 420. The symptoms 424 of one stage may correspond to an outcome 428 of another stage, which may result in different stages 420 leading to other stages 420. In some embodiments, the symptoms 424 and outcomes 428 of the stages 420 of a healthcare protocol walkthrough 400 may result in the stages 420 forming a tree (e.g., a decision tree) or a graph.

In some embodiments, the walkthrough module 118 may receive, from a user, a command to initiate a healthcare protocol walkthrough 400. The walkthrough module 118 may display data related to the healthcare protocol walkthrough 400 via the client device 120, such as the steps 426(1) of the first stage 420(1) of the healthcare protocol walkthrough 400. In some embodiments, the walkthrough protocol 116 may receive input data indicating one or more symptoms of a patient. The input data may come from the user (e.g., entering the data via the client device 120), an EHR database, a medical apparatus connected to the patient (e.g., an electrocardiograph machine), or another data source. In response to the received data, the encounter module 116 may determine an appropriate healthcare protocol walkthrough 400 for the patient and may display the selected healthcare protocol walkthrough 400 to the user.

In some embodiments, the walkthrough module 118 may display a healthcare protocol walkthrough 400 to multiple client devices 120. The walkthrough module 118 may display the healthcare protocol walkthrough 400 to the multiple client devices 120 simultaneously or at different times. For example, an emergency medical technician (EMT) may access the walkthrough module 118 via his or her client device 120, receive a healthcare protocol walkthrough 400, and display the healthcare protocol walkthrough 400 on the client device 120. The EMT may be located in an ambulance that is transporting a patient to a hospital. The EMT may perform some of the steps 426 of the healthcare protocol walkthrough 400 while in the ambulance. The walkthrough module 118 may track which steps 424 the EMT has performed. When the ambulance arrives at the hospital, the EMT may hand off the patient to an emergency room doctor. The emergency room doctor may use his or her client device 120 to access the walkthrough module 118. The emergency room doctor may receive the healthcare protocol walkthrough 400, and the healthcare protocol walkthrough 400 may show where the EMT left off in the steps 426 of the healthcare protocol walkthrough 400.

In one embodiment, the walkthrough module 118 may modify a healthcare protocol walkthrough 400 based on received data. Modifying the healthcare protocol walkthrough 400 may include adding a stage 420, step 426, outcome 428, or other data to the healthcare protocol walkthrough 400; removing a stage 420, step 426, outcome 428, or other data from the healthcare protocol walkthrough 400; or modifying a stage 420, step 426, outcome 428, or other data of the healthcare protocol walkthrough 400. In some embodiments, modifying a step 426 may include modifying the step action or level of recommendation of the step 426. The received data may include patient data (e.g., age, medical history, etc.) or other data. The modification of the healthcare protocol walkthrough 400 may be a temporary modification (e.g., only for the current instance of treating the patient).

In some embodiments, the walkthrough module 118 may retrieve healthcare protocol external data from outside the server 110. The walkthrough module 118 may modify or update a healthcare protocol walkthrough 400 based on the received data. For example, a healthcare governing body may determine that a certain step 426 in a healthcare protocol 400 is ineffective or dangerous. The server 110 may receive data from a computing device of the governing body related to the determination, and in response, the walkthrough module 118 may remove the step 426 or may mark the step as "not recommended."

Figure 5:
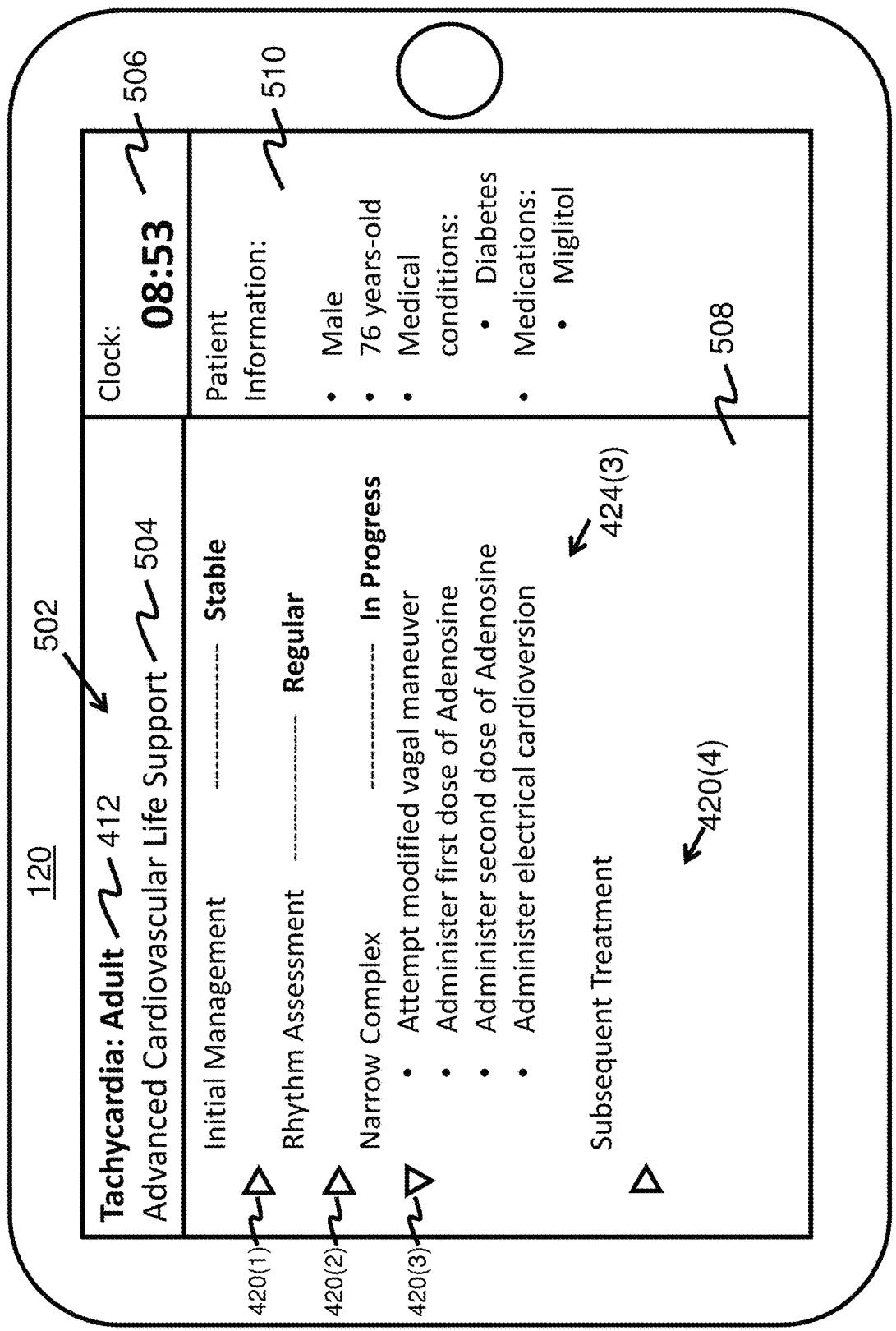
FIG. 5 is a front view illustrating an exemplary user interface for health education, certification, and recordation displayed on a client device.

FIG. 5 depicts one embodiment of a user interface for a client device 120. The user interface may display a healthcare protocol walkthrough 400. The user interface may include a header area 502. The header area 502 may include the name 412 of the healthcare protocol of the healthcare protocol walkthrough 400. The header area 502 may include other information such as a category 504 for the healthcare protocol (e.g., as depicted in FIG. 5, the healthcare protocol with the name 412 "Tachycardia: Adult" may belong to the category 504 "Advanced Cardiovascular Life Support").

In one embodiment, the user interface may include a clock area 506. The clock area 506 may include a timer. The timer may display how long a healthcare provider has been administering the healthcare protocol on the patient.

The user interface may include a steps area 508. The steps area 508 may include one or more stages 420(1)-(4). Each stage 420 may include one or more steps 426. In some embodiments, a stage 420 may be collapsible on the user interface such that only a portion of the steps 426 are visible on the user interface. For example, as depicted in FIG. 5, the stages 420(1), 420(2), and 420(4) are collapsed, and their steps 426 are not visible. However, the stage 420(3) is expanded, and its steps 426(3) are visible on the user interface. In some embodiments, the outcome of a stage 420 or step 426 may be displayed on the user interface. For example, as depicted in FIG. 5, the outcome of the first stage 420(1) is "Stable," and the outcome of the second stage 420(2) is "Regular." The user interface may also display whether a stage 420 is in progress. In some embodiments, the user interface may display whether a step 426 has been completed or an outcome of a step 426. The user interface may display a level of recommendation for a step 426.

In one embodiment, the user interface may include an auxiliary information area 510. The auxiliary information area 510 may include a variety of information. For example, as depicted in FIG. 5, the auxiliary information area 510 may display patient information, such as age, sex, known medical conditions, current medications, or other patient data. In some embodiments, the auxiliary information are 510 may display other data, such as more details about a stage 420, step 426, outcome of a stage 420 or step 426, or other data.

Certification Through Experience

Figure 6:
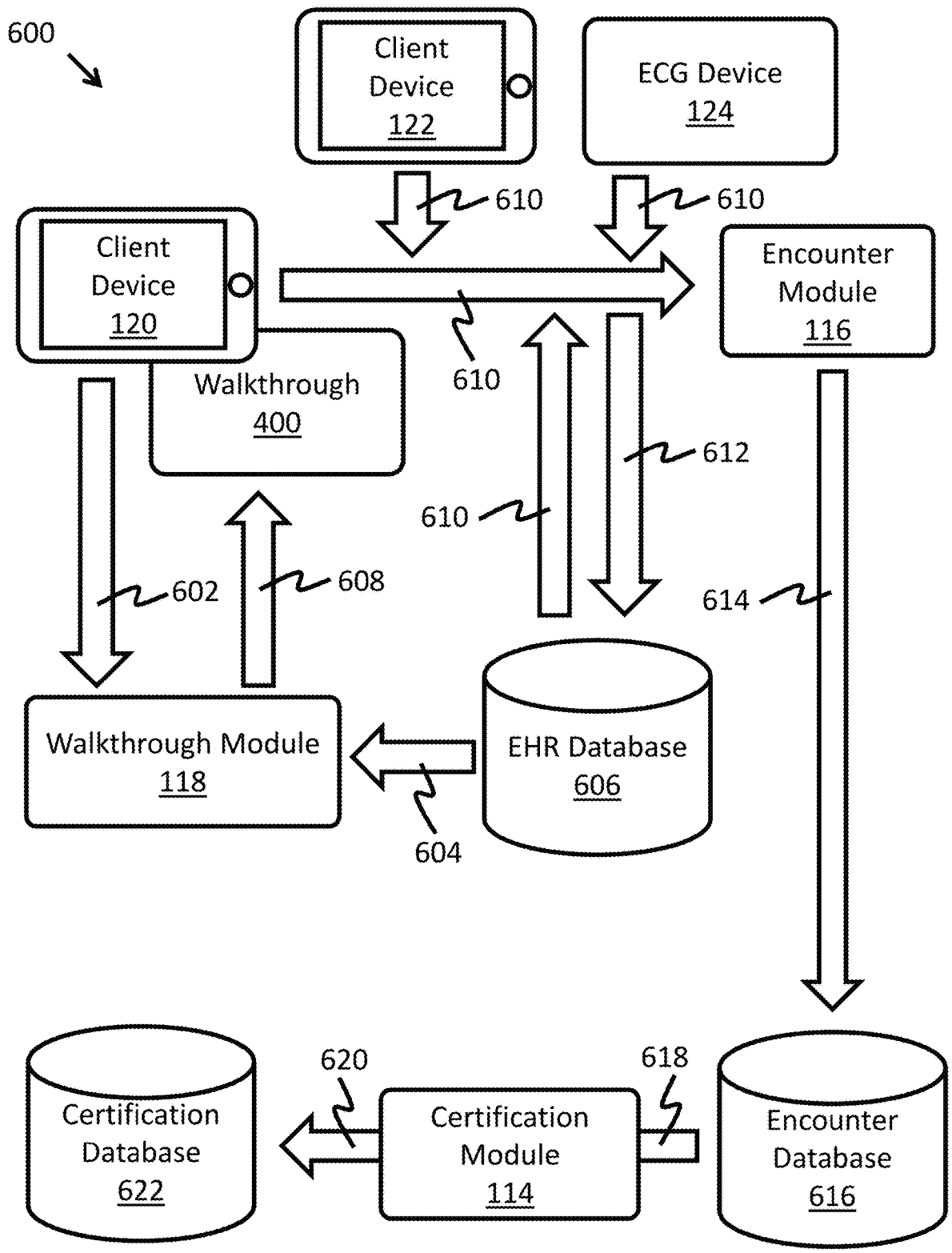
FIG. 6 is a block diagram illustrating an exemplary system for health education, certification, and recordation.

FIG. 6 depicts one embodiment of a system 600. The system 600 may provide a user the capability to work toward or maintain certification in a healthcare protocol in response to participating in a training scenario or an actual medical episode. The system 600 may include one or more components of the system 100 such as the certification module 114, encounter module 116, walkthrough module 118, or the client device 120.

In some embodiments, a training scenario or actual medical episode may begin, and a user using the client device 120 may request 602 a healthcare protocol 400 from the walkthrough module 118. The walkthrough module 118 may receive 604 data from an EHR database 606. Based on the data received from the client device 120 or the EHR database 606, the walkthrough module 118 may select or customize a healthcare protocol walkthrough 400 and send 608 the healthcare protocol walkthrough 400 to the client device 120. The user may follow the one or more steps 426 of the healthcare protocol walkthrough 400. Either during or after the training scenario or actual medical episode, the client device 120 may send 610 data to the encounter module 116. The sent data may include data indicating whether the user performed one or more steps 426 of the healthcare walkthrough 400, how well the user performed the one or more steps 426, or other data. The client device 120 may send 612 data to the EHR database 606. The encounter module 116 may generate an encounter record 300 based on the data received 610. The encounter module 116 may receive 610 data indicating whether the user performed a step 426 of the healthcare protocol walkthrough 400 and may generate an event 332 based on that data. The encounter module 116 may send 614 the encounter record 300 to an encounter database 616. The encounter database 616 may store one or more encounter records 300. The encounter database 616 may send 618 encounter data to the certification module 114. The encounter data may include an encounter record 300, a portion of an encounter record 300, or other encounter data. Based on the encounter data sent 618 by the encounter database, the certification module 114 may determine whether an event 332 of the encounter data contributes, at least in part, to a participating user completing a healthcare certification task 228(1)-(6) of a certification program 200.

In one embodiment, the request sent 602 from the client device to the walkthrough module 118 may include patient data (e.g., age, sex, patient ID, etc.). The walkthrough module 118 may customize the healthcare protocol walkthrough 400 based on the patient data (and other data, such as the data received 604 from the EHR database 606). In some embodiments, a client device 122 other than the client device 120 used by the user (e.g., a client device 112 used by a supervising physician) may send 610 at least a portion of the data. In some embodiments, another device (e.g., such as the EHR database 606, a electrocardiograph (ECG) device 124, etc.) may send 610 at least a portion of the data. In some embodiments, the client device 120 may send 610 portions of the data at different times during the training scenario or actual medical episode. Although FIG. 6 depicts the other client device 122, the EHR database 606, and the ECG device 124 sending 610 data along with the data from the client device 120, each of the other client device 122, the EHR database 606, and the ECG device 124 may send their respective data separately from the client device 120 or from each other.

The certification module 114 may determine whether an event 332 contributes, at least in part, to a participating user of the one or more participating users 214 completion of a healthcare certification task 228(1)-(6) of a certification program 200 in a variety of ways. In one embodiment, the certification module 114 may include an event-task mapping. The event-task mapping may include a data structure that maps one or more events 332 of an encounter record 300 with one or more healthcare certification tasks 228(1)-(6) of a certification program 226. In one embodiments, the certification module 114 may include a rules engine. The rules engine may include software that determines whether an event 332 contributes, at least in part, to a participating user completing a healthcare certification task 228(1)-(6).

In one embodiment, the certification module 114 may determine how a an event 332 may contribute to fulfilling a healthcare certification task 228(1)-(6). The certification module 114 may determine this based on one or more factors such as outcome of an actual medical episode (e.g., whether the user performing CPR on the patient resulted in the patient being resuscitated). The certification module 114 may determine how closely the user followed the one or more steps of the healthcare protocol walkthrough 400. The certification module 114 may use other factors or data. In some embodiments, the certification module 114 may determine that an event may contribute more (e.g., with a higher or better value) in response to the user having a successful outcome of an actual medical episode, in response to the user more closely following the one or more steps 426 the healthcare protocol walkthrough 400, or in response to the difficulty of the training scenario or actual medical episode.

In some embodiments, the certification module 114 may determine whether event 332 may contribute to fulfilling a healthcare certification task 228(1)-(6) for a user. Based on one or more configurations of the system 100 or 600, of the user's account, or other factors, the certification module 114 may determine which events 332 contribute and which events do not. For example, in one embodiment, the certification module 114 may be configured such that each event 332 contributes to fulfilling a healthcare certification task 228(1)-(6). In another embodiment, the certification module 114 may be configured such that only certain, specified events 332 contribute to a specified user's fulfillment of a healthcare certification task 228(1)-(6). In other embodiments, the certification module 114 may be configured such that only one out of every three events 332 for a specific user contribute to fulfilling that user's healthcare certification tasks 228(1)-(6).

In some embodiments, the certification module 114 may determine that an event 332 contributes to fulfilling a healthcare certification task 228(1) for a user only in response to the user currently being assigned a task group 222(1) with that healthcare certification task 228(1). For example, referring to FIG. 2B, a participating user of the one or more participating users 214 may currently be working on the healthcare certification tasks 228(2) of the task group 222(2). The participating user may resuscitate a patient using CPR during an actual medical episode. The encounter module 116 may generate an encounter record 300 based on the medical episode. The encounter module 116 may send the encounter record 300 to the certification module 114. The certification module 114 may include an event-task mapping that results in a CPR event 332 contributing to fulfilling a demonstrating CPR healthcare certification task 228(2), such as the "Demonstrate CPR basics on training mannequin" task of the one or more healthcare certification tasks 228(5) of the task group 222(5). However, because the participating user is currently working on task group 222(2) and not 222(5), the event 332 of resuscitating the patient during the actual medical may not contribute to the participating user fulfilling the healthcare certification task 228(5). In other embodiments, the certification module 114 may be configured such that an event 332 may contribute to a user fulfilling a healthcare certification task 228(5) of a task group 222(5) that the participating user is not currently assigned to. Other methods of certification module 114 determine whether an event 332 contributes to fulfilling a healthcare certification task 228(1)-(6) may also be used.

One embodiment may include a system. The system may include the server 110. The system may include a processor. The system may include a computer-readable storage medium. The computer-readable storage medium may include one or more machine-readable instructions that, when executed by the processor, cause the processor to perform one or more steps. In some embodiments, the computer-readable storage medium may include a computer memory, a persistent computer storage device (such as flash memory or a hard disk drive), or some other type of storage medium. In some embodiments, the machine-readable instructions may include the account module 112, the certification module 114, the encounter module 116, the walkthrough module 118, or some other machine-readable instructions.

In one embodiment, the one or more steps performed by the processor may include receiving, at a server, a request for a healthcare protocol walkthrough. The one or more steps may include generating, at the server, the requested healthcare protocol walkthrough. The healthcare protocol walkthrough may include one or more stages. The healthcare protocol walkthrough may include one or more steps. Each stage of the one or more stages may include at least one step of the one or more steps. The one or more steps may include sending, to a client device, at least a portion of the generated healthcare protocol walkthrough. The one or more steps may include receiving healthcare event data. The one or more steps may include determining whether a healthcare event of the healthcare event data contributes to fulfilling a healthcare certification task of a certification program.

In some embodiments, the server may include the server 110. The healthcare protocol walkthrough may include a healthcare protocol walkthrough 400. The one or more stages may include one or more stages 420(1)-(n) of the healthcare protocol walkthrough 400. The one or more steps may include one or more steps 426(1)-(n) of the healthcare protocol walkthrough 400. The client device may include a client device 120, 122. The healthcare event data may include event data 330. The healthcare event may include events 332(1)-(n). The healthcare certification task may include a healthcare certification task 228(1). The certification program may include a certification program 200.

In one embodiment, sending, to the client device 120, 122, the at least a portion of the generated healthcare protocol walkthrough 400 may include sending the at least a portion of the generated healthcare protocol walkthrough 400 to one or more client devices 120, 122. In some embodiments, receiving the healthcare event data 330 may include receiving the healthcare event data 330 from the client device 120, 122, an EHR database 606, or a medical device.

In one or more embodiments, receiving the healthcare event data 330 may include receiving data that includes an indication that the healthcare event 332(1) of the healthcare event data 330 corresponds to a simulation, or that corresponds to an actual medical episode.

In some embodiments, determining whether the healthcare event 332(1) of the healthcare event data 330 contributes to fulfilling the task 228(1) of the certification program 200 may include making the determination based on an event-task mapping. The event-task mapping may include a mapping of a healthcare event 332(1) to a task 228(1) of the certification program 200. At least a portion of the event-task mapping may be based on data received from a patient safety organization (PSO). In some embodiments, the one or more steps may further include anonymizing the healthcare event data 330 and sending the anonymized healthcare event data 330 to a PSO.

In some embodiments, the one or more steps may include, in response determining whether the healthcare event 332(1) of the healthcare event data 330 contributes to fulfilling the task 228(1) of the certification program 200, determining an amount that the healthcare event 332(1) contributes to fulfilling the task 228(1). In one embodiment, the amount may be based on a compliance with a healthcare protocol associated with the certification program 200, an outcome included in the healthcare event data 330 or the encounter record 300 associated with the event data 330, or a review by a healthcare worker received by the system.

Computer-Implemented Methods

Figure 7:
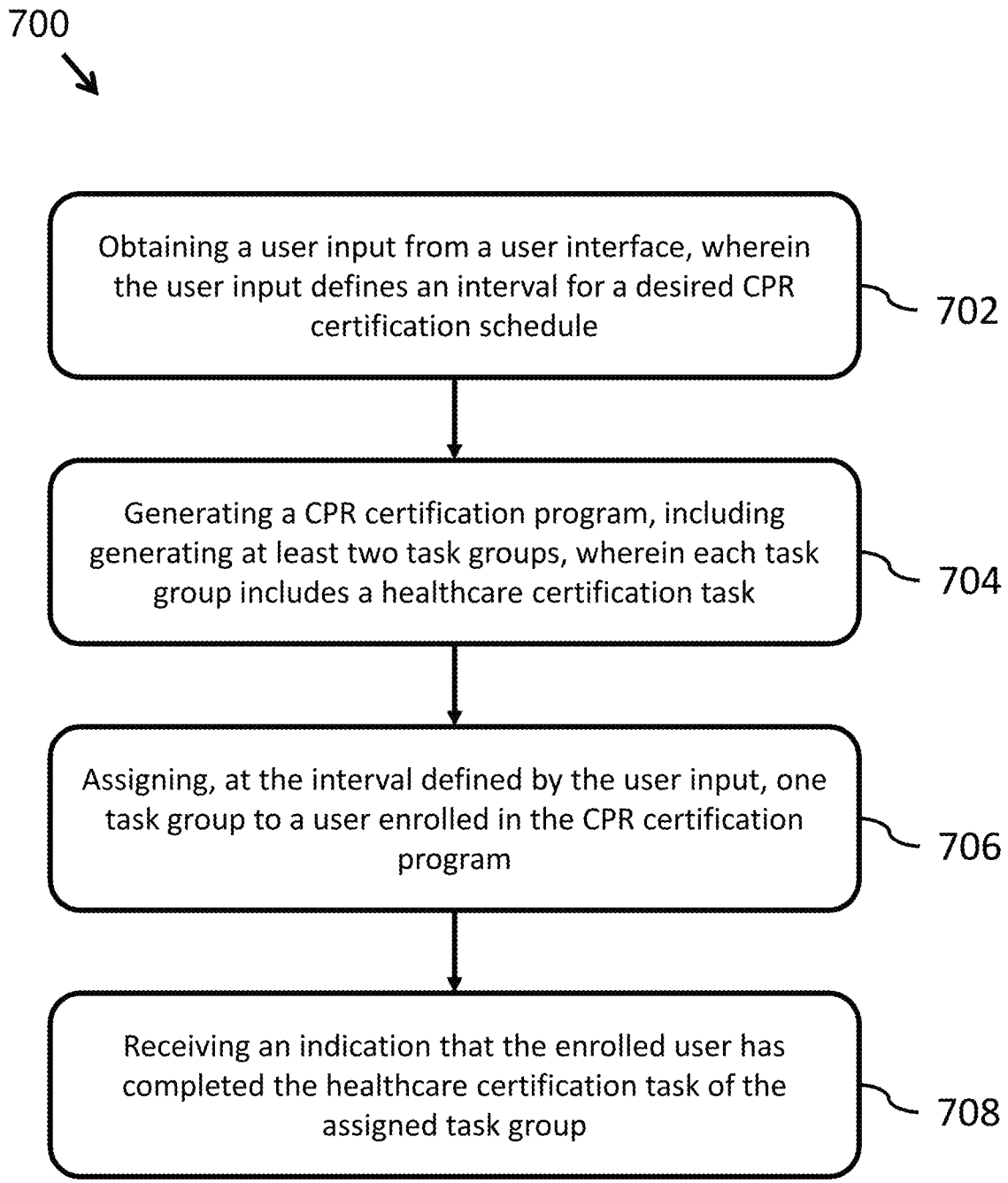
FIG. 7 is a flowchart diagram illustrating an exemplary embodiment of a method for health education, certification, and recordation.

FIG. 7 depicts one embodiment of a method 700. The method 700 may include a computer-implemented cardiopulmonary resuscitation (CPR) certification method. In one embodiment, the method 700 may include obtaining 702, at a server a user input from a user interface. The user input may define an interval for a desired CPR certification schedule. The method 700 may include generating 704, at the server, a CPR certification program. Generating 704 the CPR certification program may include generating two or more task groups. Each task group may include a healthcare certification task. The method 700 may include administering, at the server, the CPR certification program. Administering the CPR certification program may include assigning 706, at the interval defined by the user input, one task group of the two or more task groups to a user that may be enrolled in the CPR certification program. Administering the CPR certification program may include receiving 708 an indication that the enrolled user has completed the healthcare certification task of the assigned one task group.

In one embodiment, the certification module 114 may perform at least a portion of the steps 702-708 of the method 700. A certification program 200 may include the CPR certification program. In some embodiments, obtaining 702, at the server, the user input from the user interface may include receiving the user input at the server 110. The client device 120 may receive the user input from a user and may send the user input through the data network 130 to the server 110. The user input defining the interval for the desired CPR certification schedule may include a value to be used as the interval 212 of a certification program 200.

In one embodiment, generating 704 the CPR certification program may include generating a certification program 200. The certification program 200 may include a healthcare protocol 210 of "CPR." Generating the two or more task groups may include generating two or more of the task groups 222(1)-(n) of the task plan 220 pertaining to the certification program 200. The one or more healthcare certification tasks of each of the two or more task groups may include one or more healthcare certification tasks 228(1)-(n).

In some embodiments, assigning 706, at the interval defined by the user input, one task group of the two or more task groups to a user enrolled in the CPR certification program may include assigning a task group 222(1) to a participating user of the participating users 214 of the certification program 200. The certification module 114 may track users enrolled in the certification program 200 to determine which task groups 222(1)-(n) are assigned to which users, which users have completed one or more healthcare certification tasks 228(1)-(n) of the task groups 222(1)-(n), or other functionality related to users as described above.

In one or more embodiments, receiving 708 the indication that the enrolled user has completed the healthcare certification task of the assigned one task group may include the certification module 114 receiving data from the server 110, the client device 120, or another device indicating that the enrolled user has completed a healthcare certification task 228(1). The data may include data indicating whether a user viewed a video, whether a user properly performed on a training mannequin, or whether a user earned a certain score on a test, or whether a user performed some other healthcare certification task 228-completing action.

In one embodiment, generating the two or more task groups may include customizing the two or more task groups based on a specialty of a user enrolled in the CPR certification program. For example, as discussed above, to which branch the participating user may be assigned may be based on one or more characteristics of the participating user. The certification module 114 may obtain the specialty of the enrolled user from the accounts module 112 or from some other source. As another example discussed above, users enrolled in the CPR certification program may all include the same specialty (e.g. emergency room doctors), and the certification program 200 associated with that group may include one or more task groups 222(1)-(*n*) selected for that specialty.

In some embodiments, the method 700 may further include obtaining, at the server, the healthcare certification task from the American Red Cross. For example, the server 110 may receive a data representation of a healthcare certification task 228(1) over the data network 130 from a server or other computing device operated by the American Red Cross. The healthcare certification task 228(1) may be received by the certification module 114. The healthcare certification task 228(1) may be added to the library of healthcare certification tasks 228(1)-(6).

In one or more embodiments, administering the CPR certification program may further include, in response to the user completing the two or more task groups, issuing a CPR certification to the user. The user completing the two or more task groups may include the user completing the required healthcare certification tasks 228(1)-(6) of the two or more task groups 222(1)-(6) between the respective start dates 224(1)-(6) and respective end dates 226(1)-(6) of the two or more task groups 222(1)-(6) as discussed above, or may include some other action required by the certification program 200 to complete the two or more task groups.

Figure 8:
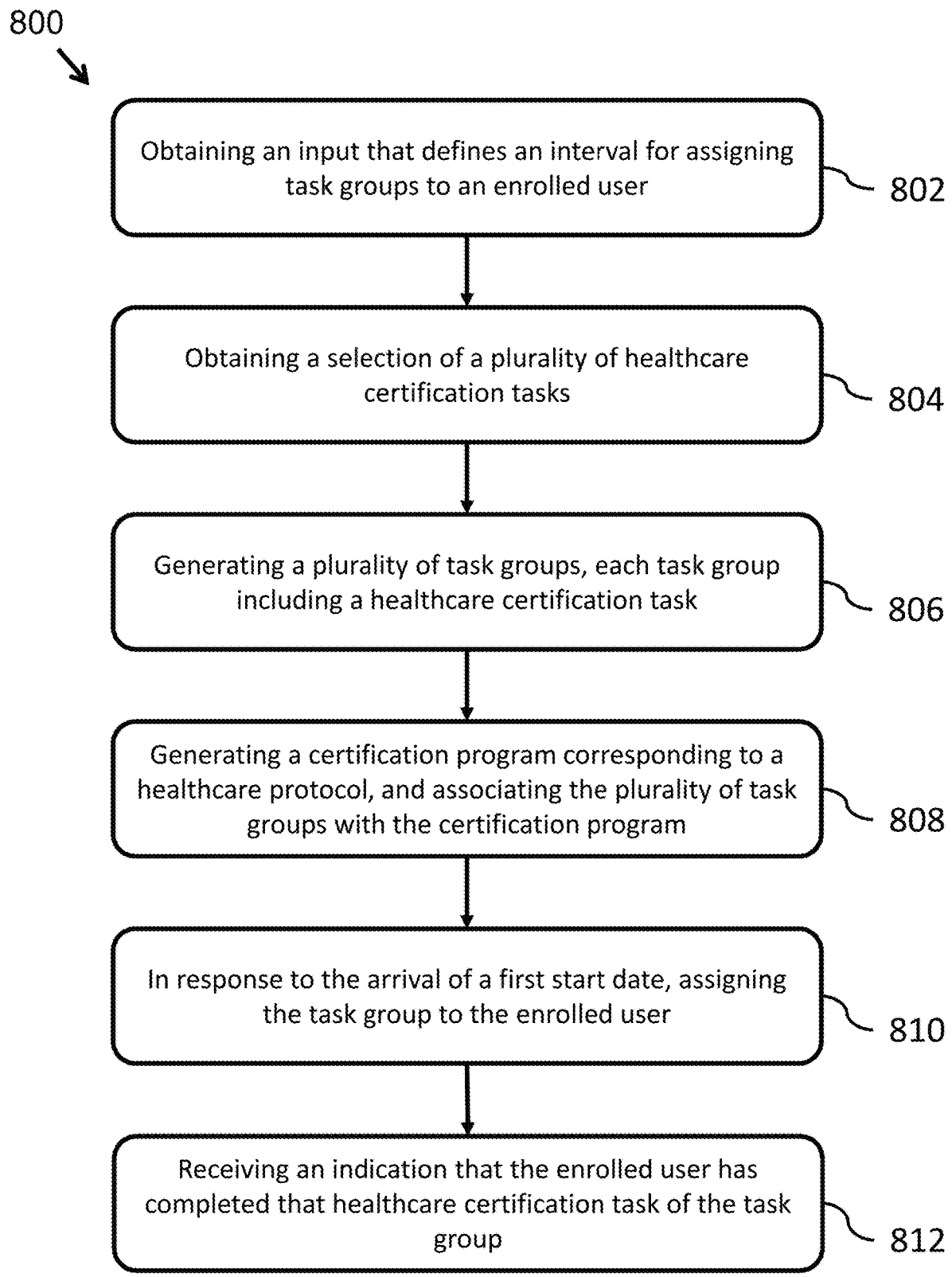
FIG. 8 is a flowchart diagram illustrating another exemplary embodiment of a method for health education, certification, and recordation.

FIG. 8 depicts one embodiment of a method 800. The method 800 may include a computer-implemented method. In one embodiment, the method 800 may include obtaining 802, at a computing device, an input that defines an interval for assigning task groups to an enrolled user. The method 800 may include obtaining 804, at the computing device, a selection of one or more healthcare certification tasks. The method 800 may include generating 806, at the computing device, one or more task groups. A task group of the one or more task groups may include a healthcare certification task of the one or more healthcare certification tasks. The method 800 may include generating 808, at the computing device, a certification program corresponding to a healthcare protocol, and associating the one or more task groups with the certification program.

In some embodiments, the method 800 may include administering, at the computing device, the certification program. Administering the certification program may include, in response to the arrival of a first start date, assigning 810, via the computing device, the task group to the enrolled user enrolled in the certification program. Administering the certification program may include receiving 812, at the computing device, an indication that the enrolled user has completed the healthcare certification task of the task group.

In one or more embodiments, the computing device may include the server 110. The interval for assigning task groups may include the interval 212. The enrolled user may include a participating user of the participating users 214. The one or more healthcare certification tasks may include the healthcare certification tasks 228(1)-(6). The one or more task groups may include task groups 222(1)-(6). The certification program may include a certification program 200.

In one embodiment, obtaining 804 the selection of the one or more healthcare certification tasks may include obtaining a selection of healthcare certification tasks 228(1)-(6) from a library of healthcare certification tasks stored by the certification module 114. In some embodiments, a certification administrator may select the healthcare certification tasks 228(1)-(6) and the certification module 114 may receive the selection of healthcare certification tasks 228(1)-(6). In another embodiment, the certification module 114 may automatically generate at least a portion of a certification program 200, which may include automatically selecting the one or more healthcare certification tasks 228(1)-(6), as described above.

In one embodiment, generating 806 the one or more task groups may include customizing the one or more task groups 222(1)-(6) based on a specialty of the enrolled user. In some embodiments, customizing the one or more task groups 222(1)-(6) based on the specialty of the enrolled user may include selecting a healthcare certification task 228(1) from the one or more healthcare certification tasks 228(1)-(6) based on the specialty of the enrolled user, and including the selected healthcare certification task 228(1) with the task group 222(1) of the one or more task groups 222(1)-(6).

In some embodiments, generating 806 the one or more task groups may include receiving, via user input received from a user interface, a selection of the healthcare certification task 228(1) from the one or more healthcare certification tasks 228(1)-(6) for inclusion with the task group 222(1) of the one or more task groups 222(1)-(6). In one embodiment, generating 806 the one or more task groups may include the computing device automatically selecting the healthcare certification task 228(1) from the one or more healthcare certification tasks 228(1)-(6) for inclusion with the task group 222(1) of the one or more task groups 222(1)-(6).

In one or more embodiments, assigning 810 the task group of the one or more task groups to the enrolled user may include assigning the task group 222(1) to the one or more enrolled users of the enrolled users group 214. In one embodiment, the enrolled users group 214 may include one or more users that include a common characteristic. The common characteristic may include a specialty, a healthcare worker position, or whether the enrolled users group includes one or more healthcare workers.

Figure 9:
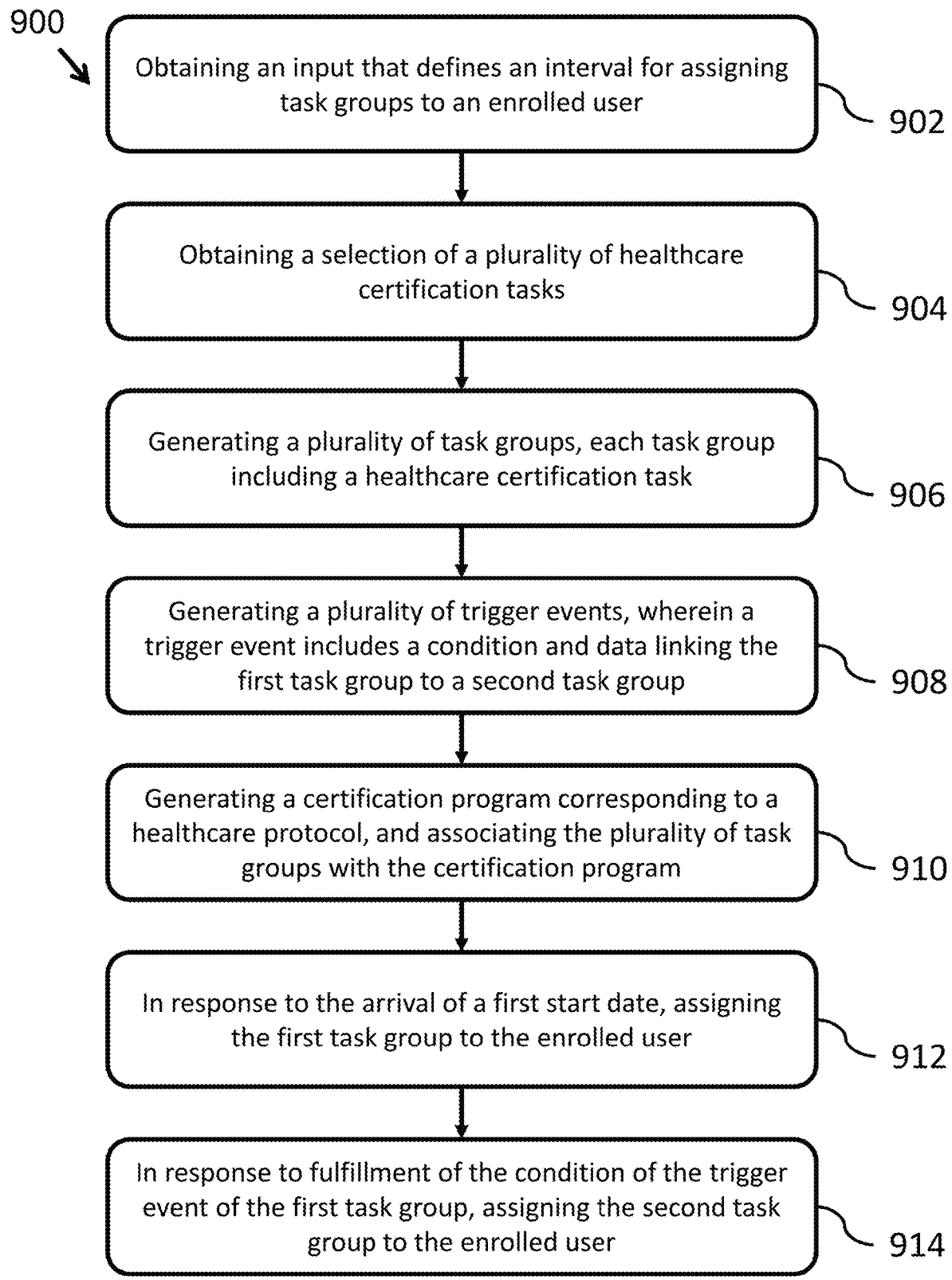
FIG. 9 is a flowchart diagram illustrating another exemplary embodiment of a method for health education, certification, and recordation.

FIG. 9 depicts one embodiment of a method 900. The method 900 may include a computer-implemented method. The method 900 may include obtaining 902, at a server, an input that defines an interval for assigning task groups to an enrolled user. The method 900 may include obtaining 904, at the server, a selection of one or more healthcare certification tasks. The method 900 may include generating 906, at the server, one or more task groups. A task group of the one or more task groups may include a healthcare certification task of the one or more healthcare certification tasks.

The method 900 may include generating 908 one or more trigger events. A trigger event of the one or more trigger events may include a condition and data linking a first task group of the one or more task groups to a second task group of the one or more task groups. The method 900 may include generating 910, at the server, a certification program corresponding to a healthcare protocol. Generating 910 the certification program may include associating the one or more task groups with the certification program. The method 900 may include administering, at the server, the certification program. Administering the certification program may include, in response to the arrival of a first start date, assigning 912 the first task group to the enrolled user enrolled in the certification program. Administering the certification program may include, in response to fulfillment of the condition of the trigger event of the first task group, assigning 914 the second task group to the enrolled user.

In some embodiments, the server may include the server 110. The interval for assigning task groups may include the interval 212. The one or more healthcare certification tasks may include the healthcare certification tasks 228(1)-(6).

The one or more task groups may include task groups 222(1)-(6). The one or more trigger events may include the trigger events 230(1)-(2). The certification program may include a certification program 200. The first start data may include the start date 224(1). The first task group may include the task group 222(1). The second task group may include the task group 222(2).

In one embodiment, the condition may include the enrolled user completing at least a portion of the healthcare certification tasks 228(1) of the first task group 222(1). In some embodiments, the condition may include an arrival of a due date 226(1) of the first task group 222(1). In one embodiment, the condition may include the enrolled user earning below a threshold score on a healthcare certification task 228(1) of the first task group 222(1). In one or more embodiments, the condition may include a specialty of the enrolled user.

Figure 10:
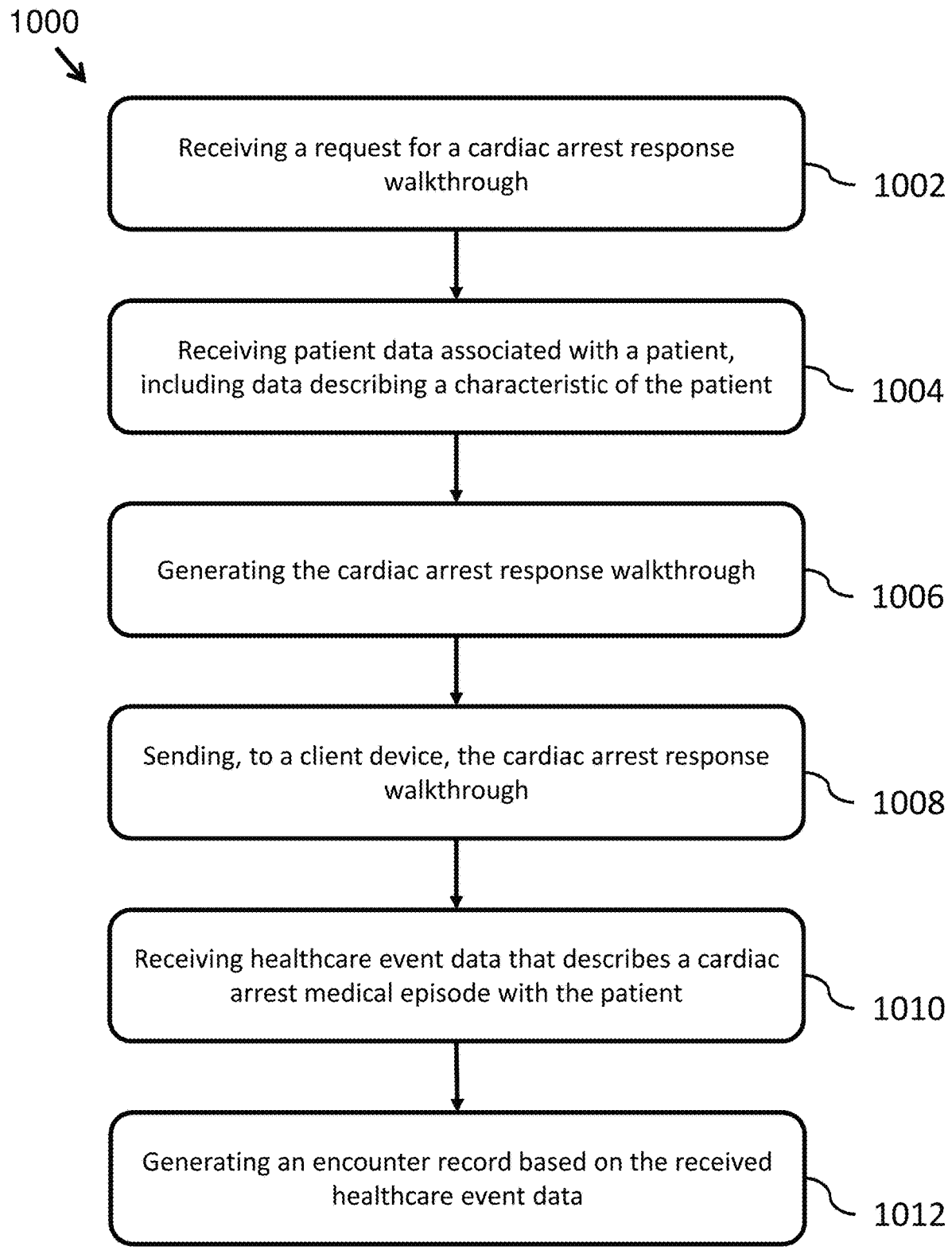
FIG. 10 is a flowchart diagram illustrating another exemplary embodiment of a method for health education, certification, and recordation.

FIG. 10 depicts one embodiment of a method 1000. The method 1000 may include a computer-implemented cardiac arrest response walkthrough method. In one embodiment, the method 1000 may include receiving 1002, at a server, a request for a cardiac arrest response walkthrough. The method 1000 may include receiving 1004, at the server, patient data associated with a patient. The patient data may include data describing a characteristic of the associated patient.

In some embodiments, the method 1000 may include generating 1006, at the server, the cardiac arrest response walkthrough. The cardiac arrest response walkthrough may include one or more cardiac arrest response steps. The server may customize the one or more cardiac arrest response steps based on the patient data. The method 1000 may include sending 1008, to a client device, the cardiac arrest response walkthrough. The method 1000 may include receiving 1010 healthcare event data that describes a cardiac arrest medical episode with the patient. The method 1000 may include generating 1012 an encounter record based on the received healthcare event data. The encounter record may include one or more cardiac arrest events associated with the patient.

In one or more embodiments, the server may include the server 110. In some embodiments, the encounter module 116 or the walkthrough module 118 may perform one or more of the steps 1002-1012 of the method 1000. The cardiac arrest response walkthrough may include a healthcare protocol walkthrough 400. The healthcare protocol name 412 may include cardiac arrest. In one embodiment, the patient data may include the patient information that may be displayed in the auxiliary information area 510. The patient data may be sent by an EHR database 606, a client device 120, 122, or by another data source. The one or more cardiac arrest response steps may include one or more steps 426(1)-(n). The healthcare event data may include the event data 330 of an encounter record 300. The one or more cardiac arrest events may include one or more events 332(1)-(n).

In some embodiments, receiving 1002 the request for the cardiac arrest response walkthrough may include receiving the request from a mobile device of a healthcare worker. The mobile device may include a client device 120. In one embodiment, receiving 1004 the patient data associated with the patient may include receiving the patient data from the mobile device. In one or more embodiments, customizing the one or more cardiac arrest response steps based on the patient data may include the server 110 customizing the one or more cardiac arrest response steps 426(1)-(n) based on the patient's age.

In one embodiment, the encounter record, which may include the encounter record 300, may include data indicating the encounter record 300 is associated with a cardiac arrest healthcare protocol (i.e., the healthcare protocol name 324 may include "Cardiac Arrest") and an outcome 316 of the cardiac arrest medical episode. In some embodiments, the method 1000 may further include determining, based on an event-task mapping, whether a healthcare event 332(1) of the healthcare event data 330 contributes to fulfilling a healthcare certification task 228(1) of a cardiac arrest certification program 200.

Figure 11:
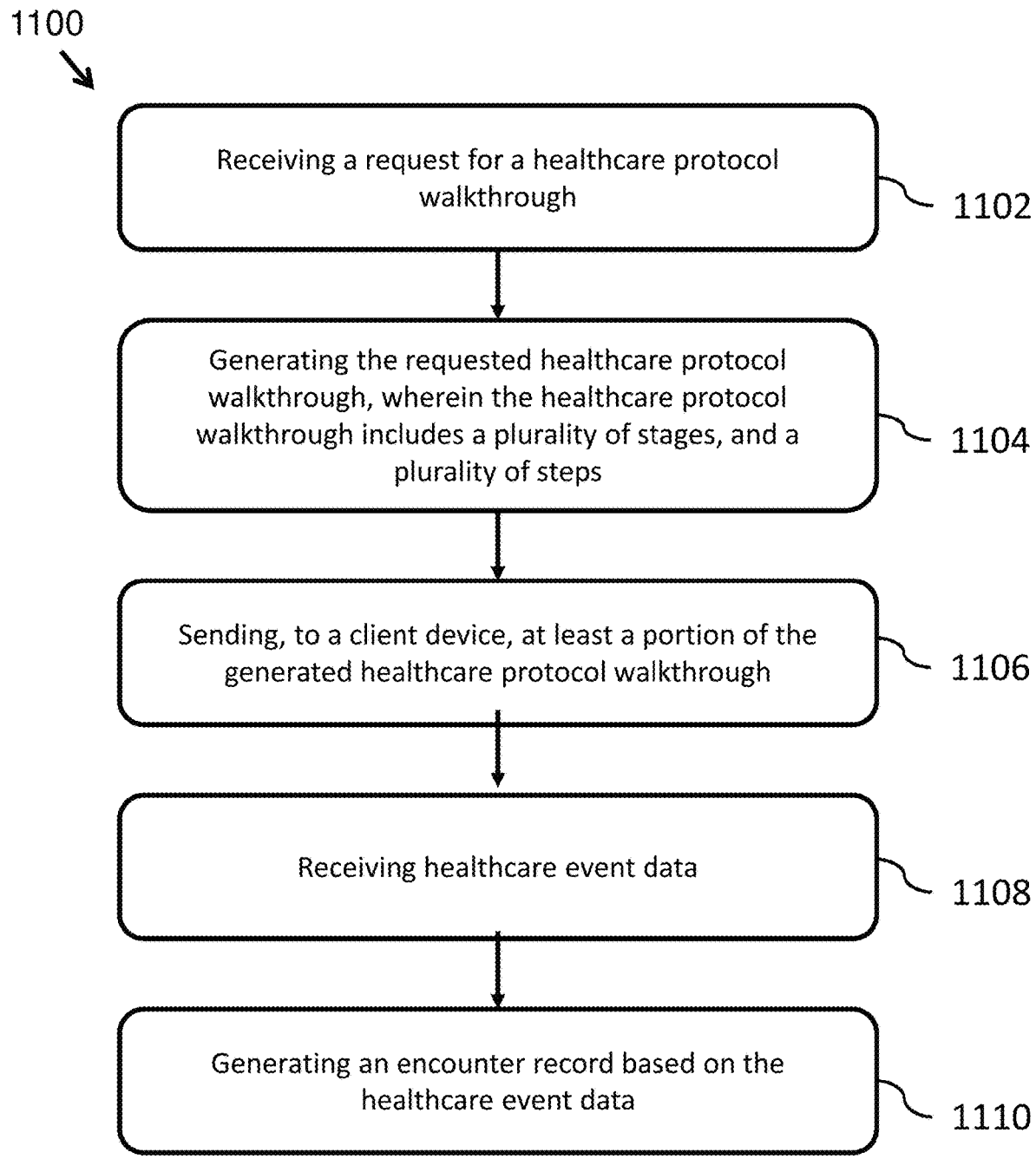
FIG. 11 is a flowchart diagram illustrating another exemplary embodiment of a method for health education, certification, and recordation.

FIG. 11 depicts one embodiment of a method 1100. The method 1100 may include a computer-implemented method. The method 1100 may include receiving 1102, at a server, a request for a healthcare protocol walkthrough. The method 1100 may include generating 1104, at the server, the requested healthcare protocol walkthrough. The healthcare protocol walkthrough may include one or more stages. The healthcare protocol walkthrough may include one or more steps. Each stage of the one or more stages may include at least one step of the one or more steps.

The method 1100 may include sending 1106, to a client device, at least a portion of the generated healthcare protocol walkthrough. The method 1100 may include receiving 1108 healthcare event data. The method 1100 may include generating 1110 an encounter record based on the healthcare event data. The encounter record may include one or more healthcare events.

In some embodiments, the server may include the server 110. The healthcare protocol walkthrough may include a healthcare protocol walkthrough 400. The one or more stages may include one or more stages 420(1)-(n) of the healthcare protocol walkthrough 400. The one or more steps may include one or more steps 426(1)-(n) of the healthcare protocol walkthrough 400. The client device may include a client device 120, 122. The healthcare event data may include event data 330. The encounter record may include an encounter record 300. The healthcare events may include events 332(1)-(n).

In some embodiments, the method 1100 may further include receiving patient data associated with a patient. Receiving the patient data associated with the patient may be similar to receiving 1004, at the server, patient data associated with a patient as described in relation to the method 1000 of FIG. 10. Generating 1104 the requested healthcare protocol walkthrough may further include selecting at least a portion of the one or more steps 426(1)-(n) based on the patient data.

In one or more embodiments, receiving the patient data associated with the patient may include receiving the patient data from a client device 120, 122 or an electronic health record (EHR) database 606. The patient data associated with the patient may include the patient's age, the patient's sex, or at least a portion of the patient's medical history. In some embodiments, receiving 1108 the healthcare event data may include receiving the healthcare event data 330 from the client device 120, 122, an EHR database 606, or a medical device. The medical device may include an electrocardiograph (ECG) device 124, a respiratory monitoring device, a pacemaker, or some other type of medical device.

Some of the steps of the above-described methods 700, 800, 900, 1000, 1100 have been described above. In some embodiments, other elements of the systems 100 or 600 may perform one or more of those steps, not just those described in relation to the methods 700, 800, 900, 1000, 1100. For example, in some embodiments, a client device 120, 122 may perform one or more of the steps of the method 700, 800, 900, 1000, 1100. In one or more embodiments, a step of a method 700, 800, 900, 1000, 1100 may include sub-steps or functionality described above in relation to FIGS. 1-6, although not explicitly described in relation to FIGS. 7-11.

Healthcare Education Simulation

In one embodiment, the systems and methods disclosed herein may provide for one or more healthcare education simulations. A healthcare education simulation may include a training medical scenario designed to educate a user or provide a user the opportunity to practice medical procedures, protocols, or other medical functions. The healthcare education simulation may include a role-based or specialty-based scenario aligned with the user's area of practice, membership in a healthcare team, or other characteristic of the user. The healthcare education simulation may include an interactive, case-based scenario that the user might encounter in his or her medical practice. In some embodiments, a user's participation in the one or more healthcare education scenario may assist the user in developing medical competence or skills in observation and decision-making during a medical event.

Figure 12:
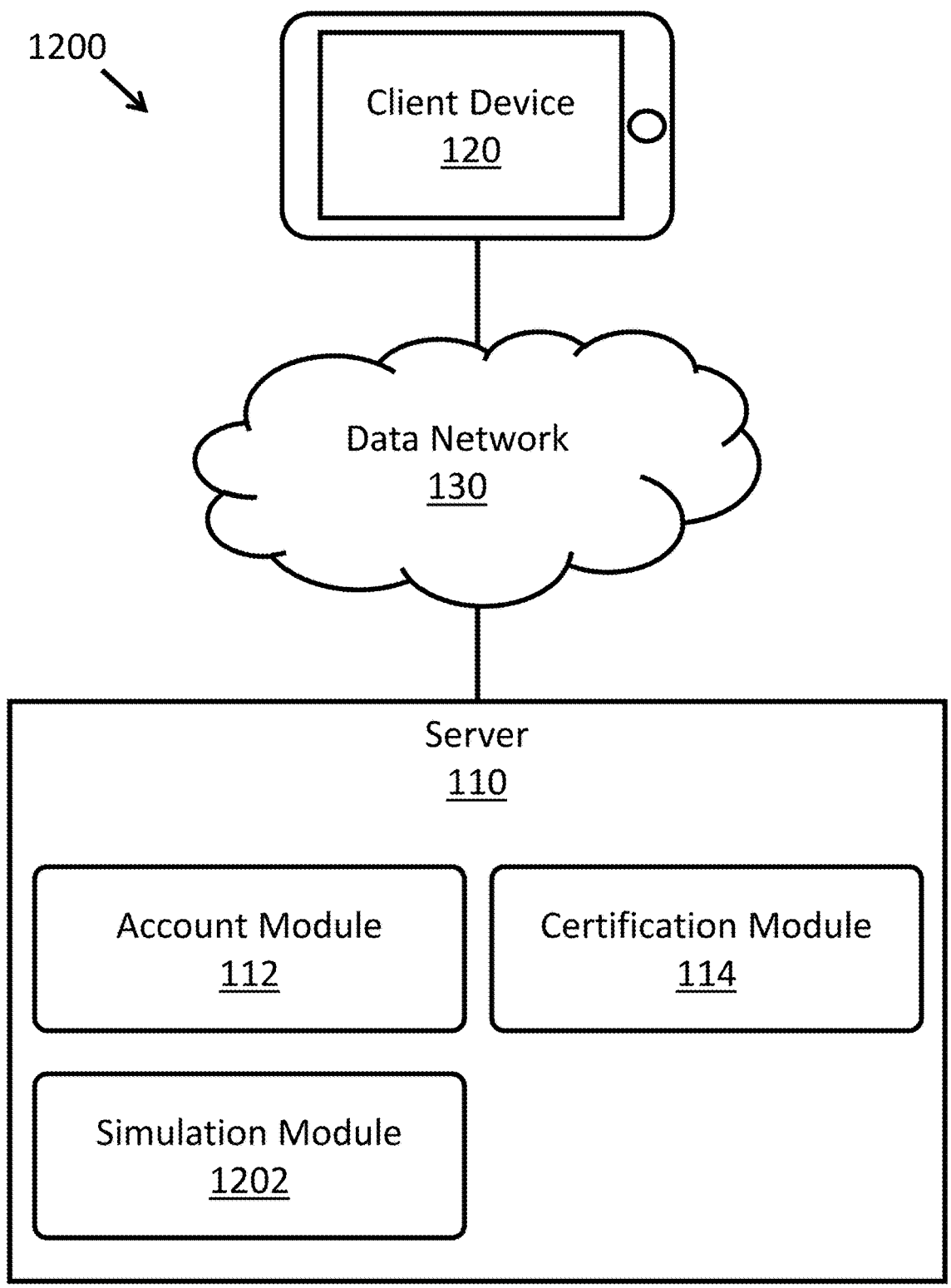
FIG. 12 is a schematic block diagram illustrating an exemplary system for health education, certification, and recordation.

FIG. 12 depicts one embodiment of a system 1200. The system 1200 may include a system for healthcare education simulation. The system 1200 may include the server 110. The server 110 may include one or more computer processors. The server 110 may include one or more non-transitory computer-readable storage media. The non-transitory computer-readable storage media may store computer-readable instructions. In one embodiment, the computer-readable instructions may include one or more modules. For example, the computer-readable instructions may include the account module 112, the certification module 114, or a simulation module 1202. In some embodiments, the computer-readable instructions may include other modules discussed previously.

In one embodiment, the server 110 may include a simulation module 1202. The simulation module 1202 may store data associated with one or more healthcare education simulations (hereinafter, "simulations"). In one or more embodiments, the simulation module 1202 may store, configure, or process data associated with one or more simulations. A simulation may include a variety of forms. In one embodiment, a simulation may include website. A simulation may include a software application such as software executable on a laptop or desktop computer. A simulation may include a mobile application for a mobile computing device. A simulation may include a virtual reality (VR) application or augmented reality (AR) application. A simulation may include software or other functionality implemented by a training mannequin or other training equipment (e.g., crash cart, defibrillator, intravenous (IV) pole, patient monitor, oxygen supply, etc.).

In one embodiment, a simulation may include a simulated healthcare scenario. A user (e.g., a user of the client device 120) may interact with the simulated healthcare scenario. In some embodiments, the simulation may include a simulated patient experiencing a medical problem or undergoing a medical procedure. The simulation may include simulated medical workers such as physicians, nurses, or other medical workers. The simulation may include information presented to the user as text, audio, or visual elements. The user interacting with the simulation may include the user viewing the presented information in order for the user to make decisions regarding the simulation. The user interacting with the simulation may include the user interacting with the simulated patient, simulated medical workers, or simulated medical equipment.

In one embodiment, the client device 120 of the system 1200 may include a mobile computer device, a VR headset device, or an electronic healthcare training mannequin. The client device 120 may include other devices that may be used along with these previously mentioned devices, such as one or more hand-held controllers, a mouse and keyboard, a touchscreen, a microphone, speakers/headphones, or other peripheral devices.

Figure 13:
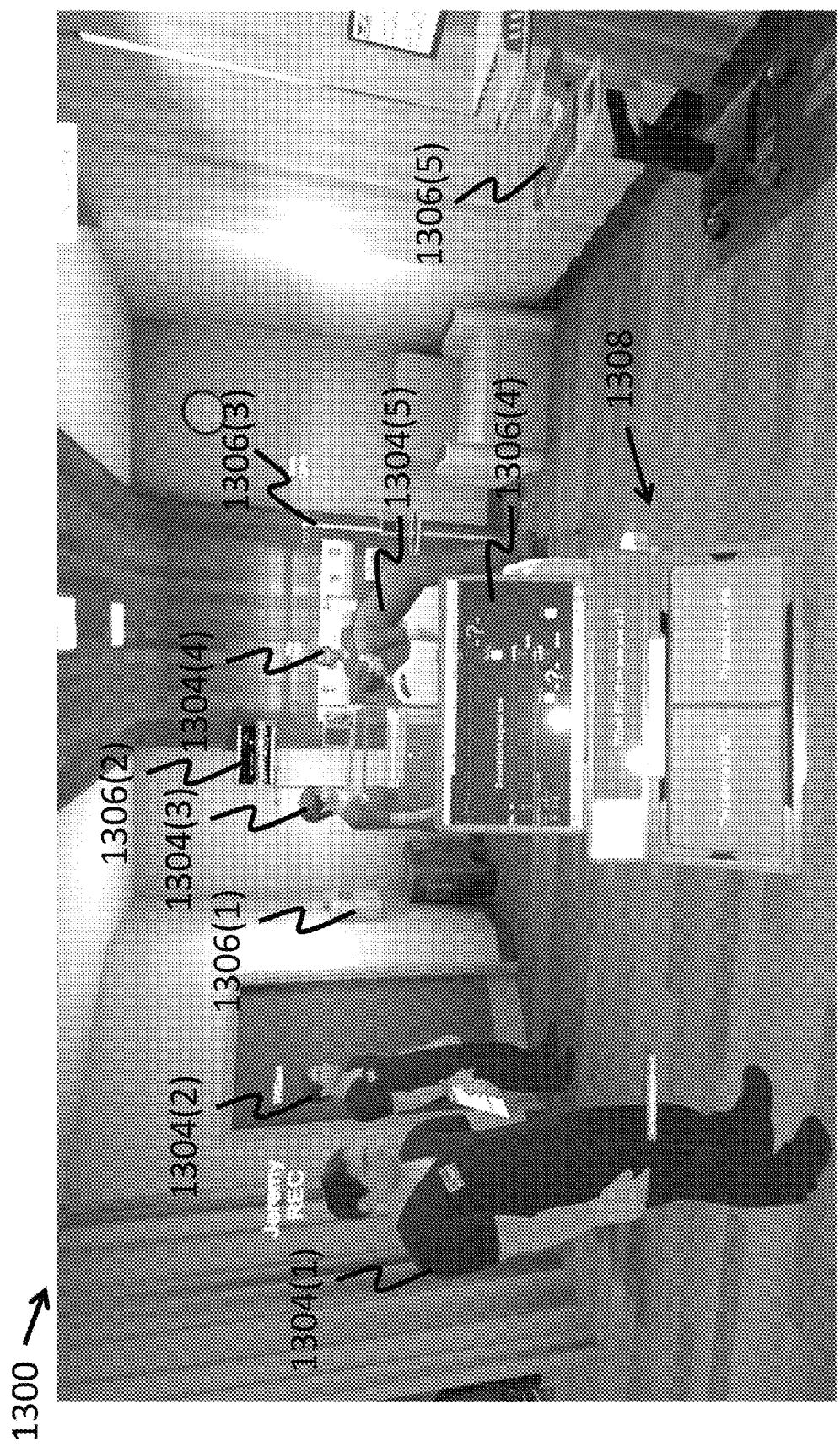
FIG. 13 is an exemplary graphical user interface of a healthcare education scenario simulation for health education, certification, and recordation.

FIG. 13 depicts one embodiment of a graphical user interface (GUI) 1300. The GUI 1300 may include a GUI for a VR application that includes one or more simulations. The GUI 1300 may depict a graphical representation of the simulation. The GUI 1300 may be displayed in a VR headset. The VR application may receive the simulation from the server 110 (via Internet streaming, file download, or some other transfer functionality). The healthcare worker user may interact with the VR application using the client device 120.

In one embodiment, the GUI 1300 may include a simulated patient (not depicted), one or more simulated medical workers 1304(1)-(5), and simulated medical equipment 1306(1)-(5). For example, the simulated medical equipment 1306(1)-(5) may include an AED 1306(1), a first patient monitor 1306(2), an IV pole 1306(3), a second patient monitor 1306(4), a mobile medical cart 1306(5), or other simulated medical equipment. Some of the simulated medical equipment 1306(1)-(5), such as the first or second patient monitors 1304(2), 1306(4) or mobile medical cart 1306(5) may present information to the healthcare worker user. The healthcare worker user may receive audio about events occurring in the simulation, such as the simulated patient or simulated medical workers 1304(1)-(5) speaking. The healthcare worker user may use the hand-held controllers to interact with the simulation, such as moving around in the scenario or operating simulated medical equipment 1306(1)-(5). The healthcare worker user may speak into the microphone to give commands to the simulated patient or simulated medical workers 1304(1)-(5).

In some embodiments, the GUI 1300 may include a question and answer (Q&A) interface 1308. The Q&A interface 1308 may include one or more questions. The Q&A interface may include one or more answers. The one or more answers may include selectable answers (e.g., multiple choice answers), a free response answer, or some other type of answer. The healthcare worker user may interact with the Q&A interface 1308 (e.g., by selecting an answer using the hand-held controllers) to answer the questions presented. Answering one or more questions may progress the simulation or cause some action in the simulation to be performed.

Figure 14:
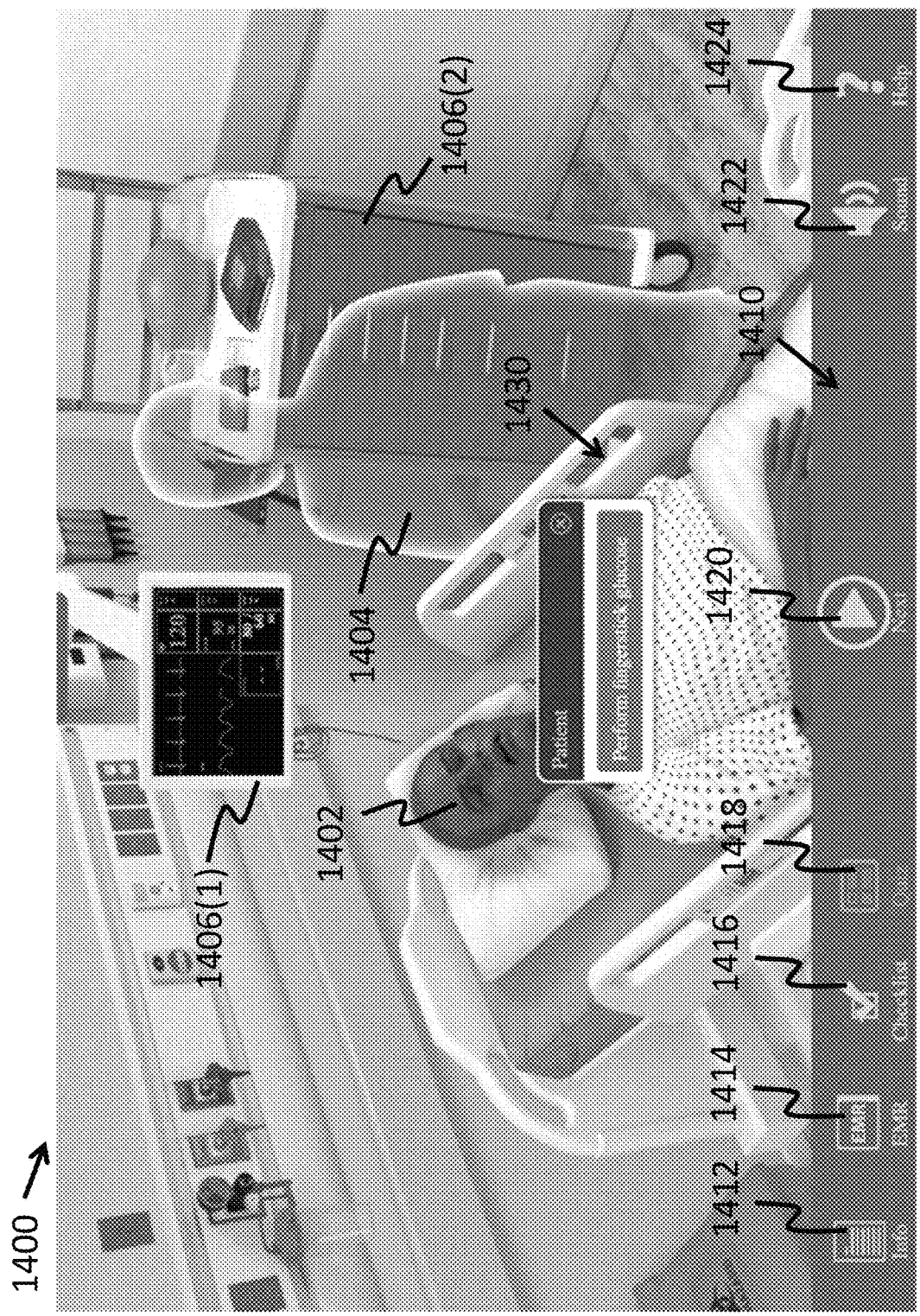
FIG. 14 is an exemplary graphical user interface of a healthcare education scenario simulation for health education, certification, and recordation.

FIG. 14 depicts one embodiment of a GUI 1400 of a software application (such as a mobile application or a desktop computer application) that includes a simulation. The GUI 1400 may present a healthcare worker user with the scenario via a touchscreen or monitor device. The healthcare worker user may view the simulation as videos, images (including computer-generated imagery), text, or audio. The GUI 1400 may include the simulated patient 1402, the one or more simulated medical workers 1404, and the simulated medical equipment 1406(1)-(2). The simulated medical equipment 1406(1)-(2) may include a patient monitor 1406(1), a medical cart 1406(2), or other simulated medical equipment. In some embodiments, the simulated patient 1402, the one or more simulated medical workers 1404, or the simulated medical equipment 1406(1)-(2) may include functionality similar to those in the GUI 1300 of FIG. 13.

In one or more embodiments, the GUI 1400 may include a control panel 1410. The control panel 1410 may include buttons or other interactive objects. The medical worker user may select the interactive objects on the control panel 1410 to cause an action to occur in the simulation. The control panel 1410 may include an information button 1412. In response to the healthcare worker user selecting the information button 1412, the GUI 1400 may display background information about the simulation. The control panel 1410 may include an electronic medical record (EMR) button 1414. In response to the healthcare worker user selecting the EMR button 1414, the GUI 1400 may display a simulated EHR of the simulated patient 1402. The control panel 1410 may include a checklist button 1416. In response to the healthcare worker user selecting the checklist button 1416, the GUI 1400 may display a checklist. The checklist may include items such as healthcare tasks the healthcare worker user should perform, observations the healthcare worker user should make, or other actions the healthcare worker user can perform in the simulation. The control panel 1410 may include a quiz button 1418. In response to the healthcare worker user selecting the quiz button 1418, the GUI 1400 may display a quiz. The quiz may include questions and answers. The quiz may relate to the simulation.

In some embodiments, the control panel 1410 may include a next button 1420. In response to the healthcare worker user selecting the next button 1420, the simulation may progress to a next portion of the scenario, may progress further in time in the scenario, or may otherwise advance the scenario. The control panel 1410 may include a sound button 1422. In response to the healthcare worker user selecting the sound button 1422, the GUI 1400 may display a volume control (e.g., a volume slider), may mute the sound of the scenario, or perform other sound functionality. The control panel 1410 may include a help button 1424. In response to the healthcare worker user selecting the help button 1424, the GUI 1400 may display information that may assist the healthcare worker user. The information that may assist the healthcare worker may include hints about the scenario, instructions on how to interact with the simulation, or other helpful information.

In one embodiment, the GUI 1400 may include one or more interaction options 1430. In response to the healthcare worker user selecting an interactive object in the simulation, an interaction option 1430 may appear. The interaction option 1430 may include a name of the interactive object the healthcare worker user selected. The interaction option 1430 may include one or more options the healthcare worker user may select. An option may include an action to be performed, a command to be given, or some other type of option. For example, as depicted in FIG. 14, in response to the healthcare worker user selecting the simulated patient 1402, the GUI 1400 may display the interaction option 1430. The interaction option 1430 may include a string of text identifying the selected object as "Patient," and the interaction option 1430 may include the option "Perform fingerstick glucose." In response to the healthcare worker user selecting the "Perform fingerstick glucose" option, the simulation may simulate a glucose fingerstick, which may affect objects or other things in the simulation. For example, the patient monitor 1406(1) or another simulated medical equipment 1406(1)-(2) may display the simulated patient's 1402 glucose level.

Figure 15:
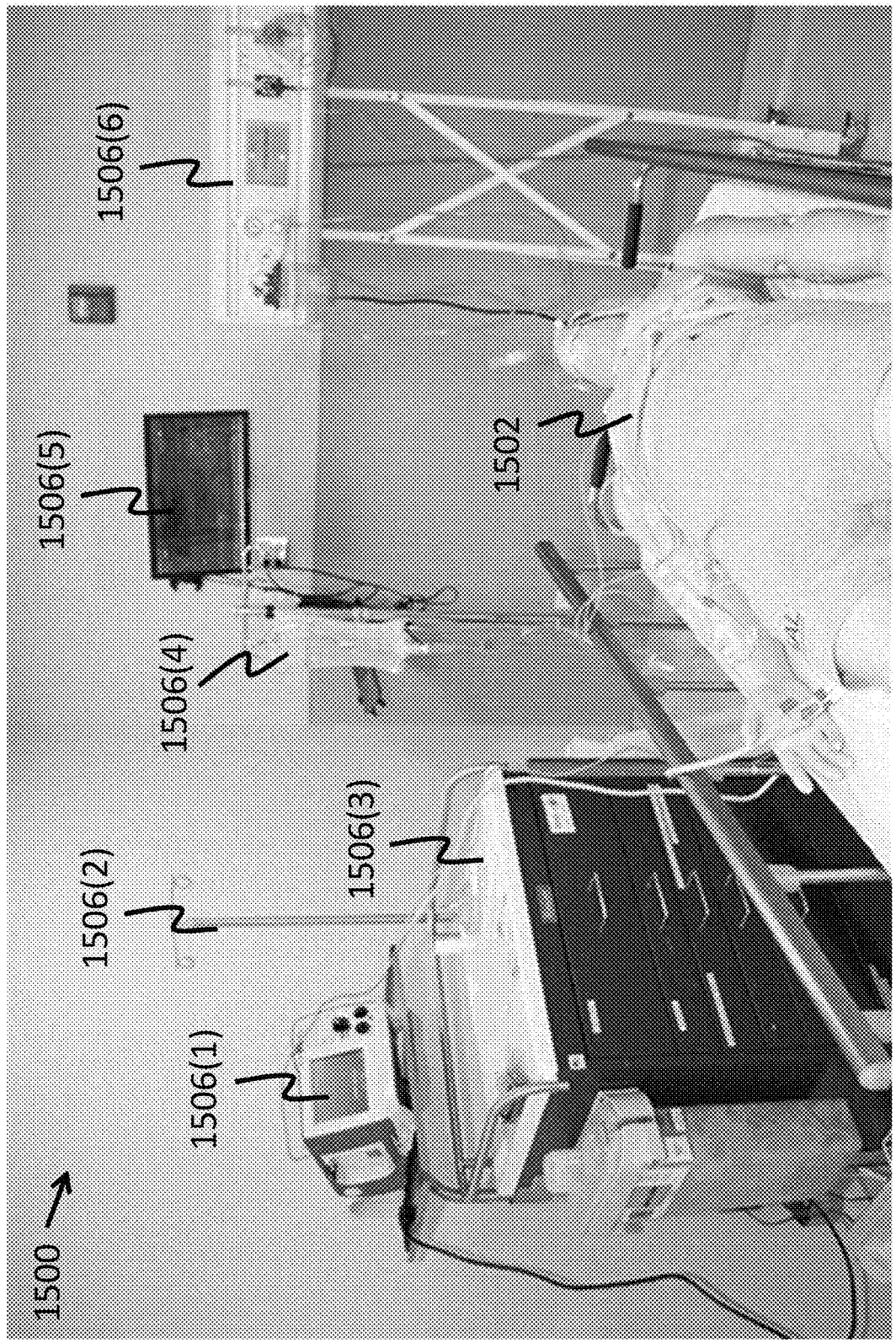
FIG. 15 is a perspective view illustrating an exemplary system of a healthcare education scenario simulation for health education, certification, and recordation.

FIG. 15 depicts one embodiment of a system 1500. The system 1500 may include a system for a simulation. The system 1500 may include a training mannequin 1502. The training mannequin 1502 may include an electronic healthcare training mannequin. The system 1500 may include simulated medical equipment 1506(1)-(6). The simulated medical equipment 1506(1)-(6) may include a defibrillator 1506(1), a first IV pole 1506(2), a crash cart 1506(3), a second IV pole 1506(4), a patient monitor 1506(5), or a wall-mounted equipment management system 1506(6). The simulated medical equipment 1506(1)-(6) may include other types of equipment. In one embodiment, the simulated medical equipment 1506(1)-(6) may include physical embodiments of medical equipment. The simulated medical equipment 1506(1)-(6) may include actual medical equipment or may include actual medical equipment that has been modified for training or simulation purposes.

In one or more embodiments, the training mannequin 1502 and simulated medical equipment 1506(1)-(6) may be in data connection with a computing device (e.g., the client device 120 or the server 110). The computing device may send data to and receive data from the training mannequin 1502 and the simulated medical equipment 1506(1)-(6). For example, the computing device may send patient monitoring data to the patient monitor 1506(5) for the healthcare worker user to view. The healthcare worker user may interact with the training mannequin 1502 (e.g., performing chest compressions on the training mannequin) and the hardware of the training mannequin 1502 may detect the interaction and send data about the interaction to the computing device.

It should be noted that some elements of the GUIs 1300 or 1400 or the system 1500 may be included in the other GUIs 1300 or 1400 or the system 1500 even if that element has not been explained in relation to the GUI or system. For example, the GUI 1300 may include the interaction option 1430 of the GUI 1400 so that the healthcare worker user may interact with elements of the GUI 1300 in a similar manner. In another example, the GUI 1400 may include the Q&A interface 1308 of the GUI 1300. In another example, the system 1500 may include a client device 120 that may include the Q&A interface 1308 of the GUI 1300.

In some embodiments, the computer-readable instructions, when executed by at least a portion of the one or more computer processors, may cause at least a portion of the one or more computer processors to perform one or more steps. The one or more steps may include storing, in one or more non-transitory computer storage devices, a plurality of healthcare worker user data records. The one or more steps may include storing, in the one or more non-transitory computer storage devices, a plurality of healthcare scenario simulation data records. The one or more steps may include receiving, from a client device 120, a request for a healthcare scenario simulation. The one or more steps may include determining, at one or more servers 110, an identity of a healthcare worker user based on the request for the healthcare scenario simulation. The one or more steps may include selecting, from the plurality of healthcare worker user data records, a first healthcare worker user data record based on the identity of the healthcare worker user. The one or more steps may include generating, at the one or more servers 110, a customized healthcare scenario simulation based on the first healthcare user data record, and at least a portion of the plurality of healthcare scenario simulation data records. The one or more steps may include transmitting the customized healthcare scenario simulation to the client device 120.

In one or more embodiments, a non-transitory computer storage device may include a hard disk, a random access memory (RAM), a flash memory, or another type of computer storage device mentioned herein. The server 110 may include the non-transitory computer storage device, or another device in data communication with the server 110 may include the non-transitory computer storage device. In some embodiments, a healthcare worker user data record may include a user account as described herein in relation to the account module 112. In some embodiments, the healthcare worker user data record may include a specialty of the healthcare worker user, a role of the healthcare worker user, or a team of the healthcare worker user. The role of the healthcare worker user may include a nurse, a medication nurse, an emergency medical technician (EMT), a physician, or some other type of healthcare worker. In one embodiment, the healthcare worker user data record may include one or more healthcare assessment results of the healthcare worker user. A healthcare assessment result of the healthcare worker user may include a score on a written test, an assessment in proficiency in a healthcare protocol made by another medical worker or by assessment software, as a result of a simulation, or some other type of assessment.

In one embodiment, a healthcare scenario simulation data record may include at least a portion of the data of a simulation. A healthcare scenario simulation data record may include image data, video data, audio data, text data, a portion of executable data, or some other type of data. In another embodiment, a healthcare scenario simulation data record may include the entire simulation data for one or more simulations. A simulation software application may combine or execute one or more healthcare scenario simulation data records in order to generate the healthcare scenario simulation. In some embodiments, the healthcare scenario simulation data record may be stored as one or more files in a file system, a database record in a database, data in computer memory, or in some other data storage format. In one embodiment, the simulation module 1202 may store the healthcare scenario simulation data records. In another embodiment, another portion of the server 110 or another device with computer storage may store the healthcare scenario simulation data records, and the simulation module 1202 may retrieve the healthcare scenario simulation data records in order to process them.

In one embodiment, generating, at the one or more servers 110, a customized healthcare scenario simulation based on the first healthcare user data record and at least a portion of the plurality of healthcare scenario simulation data records may include a variety of computer functionality. The simulation module 1202 may generate the customized healthcare scenario simulation. Generating the customized healthcare scenario simulation may include selecting scenario elements based on the first healthcare user data record. In some embodiments, scenario elements may include a simulated patient 1402, 1502, simulated medical workers 1304(1)-(5), 1404, simulated medical equipment 1306(1)-(5), 1406(1)-(2), 1506(1)-(6), healthcare tasks, interactive options, locations, healthcare problems, or other elements of a simulation. The first healthcare user data record may identify the healthcare worker user that is requesting the customized healthcare scenario simulation. The simulation module 1202 may retrieve data about the first healthcare user from the first healthcare user data record or may retrieve data about the first healthcare user from elsewhere (e.g., the account module 112 or another user data storage).

Selecting scenario elements based on the first healthcare user data record may include selecting scenario elements based on a role of the first healthcare user or a specialty of the first healthcare user. For example, the first healthcare user may be an emergency room physician, and the simulation module 1202 may include a simulated patient 1402 (which may include the training mannequin 1502) experiencing a heart attack, blood loss, or some other medical emergency.

In one embodiment, generating the customized healthcare scenario simulation may include including, in the simulation, a plurality of healthcare tasks based on the first healthcare user data record. The plurality of healthcare tasks may be based on the first healthcare user's specialty or role. For example, a nurse user may have different healthcare tasks than a physician user. An emergency room physician may have different tasks than a surgeon. Generating the customized healthcare scenario simulation may include including, in the simulation, a plurality of healthcare questions. The healthcare questions may include questions about the first healthcare user's observations in the scenario, questions about what the first healthcare user should do next in the scenario, or other questions. The first healthcare user may respond to these questions via the client device (e.g., selecting an option using a hand-held controller or touch-screen). The questions or responses may be included in the Q&A interface 1308. Generating the customized healthcare scenario simulation may include including, in the simulation, a healthcare problem exhibited by a virtual patient. For example, the healthcare problem may include the simulated patient 1402 experiencing a heart attack, tachycardia, bradycardia, or some other medical condition. The healthcare problem may include the simulated patient 1402 needing surgery, a certain medical procedure, or a certain medication. In some embodiments, the customized healthcare scenario simulation may not directly present the healthcare problem to the first healthcare user. Instead, the first healthcare user may need to deduce the healthcare problem based on information presented in the simulation.

Figure 16B:
FIG. 16B is a flowchart diagram illustrating another exemplary embodiment of a method for health education, certification, and recordation.

FIGS. 16A-B depict one embodiment of a method 1600. The method 1600 may include a computer-implemented healthcare education simulation method. In one embodiment, the method 1600 may include storing 1602, in one or more non-transitory computer storage devices, a plurality of healthcare worker user data records. The method 1600 may include storing 1604, in the one or more non-transitory computer storage devices, a plurality of healthcare scenario simulation data records. The method 1600 may include receiving 1606, from a client device, a request for a healthcare scenario simulation. The method 1600 may include determining 1608, at one or more servers, an identity of a healthcare worker user based on the request for the healthcare scenario simulation. The method 1600 may include selecting 1610, from the plurality of healthcare worker user data records, a first healthcare worker user data record based on the identity of the healthcare worker user. The method 1600 may include generating 1612, at the one or more servers, a customized healthcare scenario simulation based on the first healthcare user data record, and at least a portion of the plurality of healthcare scenario simulation data records. The method 1600 may include transmitting 1614 the customized healthcare scenario simulation to the client device.

In some embodiments, generating 1612, at the one or more servers, the customized healthcare scenario simulation may be further based on historical training data, clinical data, adaptive training data or baseline results. The historical training data or baseline results may include data received from a patient safety organization (PSO). The historical training data may include the results from training multiple healthcare workers. For example, historical training data may include data showing that many new healthcare workers are not proficient in CPR. Generating 1612 the customized healthcare scenario simulation may include a higher likelihood of including CPR-related training in the simulation based on that historical training data. Baseline results may include the results the healthcare worker user obtained in a first simulation. Baseline results may include the results of one or more other healthcare worker users. The simulation module 1202 may compare the healthcare worker user's results of a recent simulation to the baseline results to show where the healthcare worker user has improved or declined or where the healthcare worker user should focus his or her efforts.

In one embodiment, the method 1600 may further include receiving, from the client device, a result of the healthcare scenario simulation at the one or more servers. In some embodiments, after the healthcare worker user has used the client device 120 to perform a simulation, the client device 120 may send one or more results to the server 110. A result of the simulation may include whether the healthcare worker user observed a certain phenomenon in the simulation, whether the healthcare worker user deduced a healthcare problem presented in the simulation, whether the healthcare worker user completed one or more healthcare tasks, a time elapsed in the simulation (e.g., the time it took for the healthcare worker user to complete a healthcare task or complete the simulation), whether the healthcare worker user solved the healthcare problem, whether the healthcare worker user performed correct or incorrect actions during the simulation, or other results.

In some embodiments, the method 1600 may further include updating a progress of the healthcare worker user in a healthcare protocol certification program based on the result of the healthcare scenario simulation. The healthcare worker user may be a participating user 214 in a certification program 200. The simulation module 1202 may receive a result about the healthcare worker user's performance in a simulation. The simulation module 1202 may send the result to the certification module 114. The certification module 114 may process the result and determine that the result at least partially completes one or more healthcare certification tasks 228(1) in the task plan 220 of the certification program 200 that the healthcare worker user is enrolled in.

As an example, the healthcare worker user participates in a certification program 200 where the healthcare protocol 210 is CPR. The healthcare work user participates in a healthcare scenario simulation where the healthcare worker user correctly performed CPR on the simulated patient 1402, 1502. The simulation module 1202 may receive the result that the healthcare worker user correctly performed CPR. In response, the simulation module 1202 may send the result to the certification module 114. The certification module 114 may determine that the result maps to a healthcare certification task 228(5) that included demonstrating CPR. In response, the certification module 114 may update the healthcare certification task 228(5) as complete. In some embodiments, updating the progress of the healthcare worker user in a certification program 200 based on the result of the healthcare scenario simulation may be similar to updating the progress of the healthcare worker user in the certification program 200 based on the result of an actual medical episode as described above in relation to FIG. 6.

As an example of the method 1600, the server 110 may store 1602, in one or more non-transitory computer storage devices of the server 110, a plurality of healthcare worker user data records. The account module 112 may have access to these healthcare worker user data records. The server 110 may also store 1604, in the one or more non-transitory computer storage devices of the server 110, a plurality of healthcare scenario simulation data records. The simulation module 1202 may have access to these healthcare scenario simulation data records.

The client device 120 may include a desktop computer with a VR headset and hand-held controllers. The desktop computer may include a VR application for simulations, and the VR application may be installed on the desktop computer. A healthcare worker user may run the VR application on the desktop computer and put on the VR headset and hand-held controllers. The healthcare worker user may use the VR headset and hand-held controllers to request a healthcare scenario simulation. The VR application may communicate with the server 110 via the data network 130 to send the request to the simulation module 1202. The request may include an identifier that uniquely identifiers the healthcare worker user. The simulation module 1202 may receive 1606 the request for the healthcare scenario simulation from the desktop computer. The simulation module 1202 may send the identifier found in the request to the account module 112.

The account module 112 may determine 1608 the identity of the healthcare worker user based on the identifier. The identifier may include a username or an ID number (e.g., an employee ID number) of the healthcare worker user. The account module 112 may use the identifier to find a matching identifier in an account database. Once the matching user account for the healthcare worker user is found in the account database, the account module 112 may select 1610, from the plurality of healthcare worker user data records in the account database, a first healthcare worker user data record. The first healthcare worker user data record may correspond to the healthcare worker user using the client device 120. The account module 112 may send at least a portion of the first healthcare worker user data record to the simulation module 1202.

The simulation module 1202 may process the at least a portion of the first healthcare worker user data record to determine a specialty, role, and team of the healthcare worker user. The processing may include the simulation module 1202 determining that the healthcare worker user is an emergency room physician on the resuscitation team of a hospital. In response to making these determinations, the simulation module 1202 may generate 1612 a customized healthcare scenario simulation. The customized healthcare scenario simulation may be customized for an emergency room worker, a physician, or a resuscitation team member. For example, the customized healthcare scenario simulation may include a scenario in an emergency room. The scenario may include a simulated patient 1402 that is experiencing a heart attack. The scenario may include one or more simulated medical workers 1304(1)-(5), 1404 that are on the resuscitation team. One of the simulated medical workers 1304(1)-(5), 1404 may include a resuscitation team leader that may give the healthcare worker user commands or tasks during the simulation. The simulation module 1202 may include resuscitation-related tasks for the healthcare worker user to complete during the simulation, such as resuscitating or stabilizing the simulated patient 1402. The tasks may include one or more sub-steps, such as performing chest compressions, checking vital signs, etc.

The simulation module 1202 may send the files that make up the customized healthcare scenario simulation to the client device 120 via the data network 130. The client device 120 may receive the files. The VR application may use the files to execute the customized healthcare scenario simulation. The simulation may appear on the VR headset as the GUI 1300 or 1400. The healthcare worker user may participate in the simulation and successfully resuscitate the simulated patient 1402. During or after the simulation, the client device 120 may send results from the simulation to the simulation module 1202. The results may include that the healthcare worker user successfully resuscitated the simulated patient 1402. The simulation module 1202 may send the results to the certification module 114. The certification module 114 may determine whether the healthcare worker user is enrolled in a CPR certification program 200, determine whether the results correspond to a healthcare certification task 228(5) that requires demonstration of CPR skills, and update the healthcare worker user's progress in the certification program 200 based on the successful resuscitation.

Figure 17A:
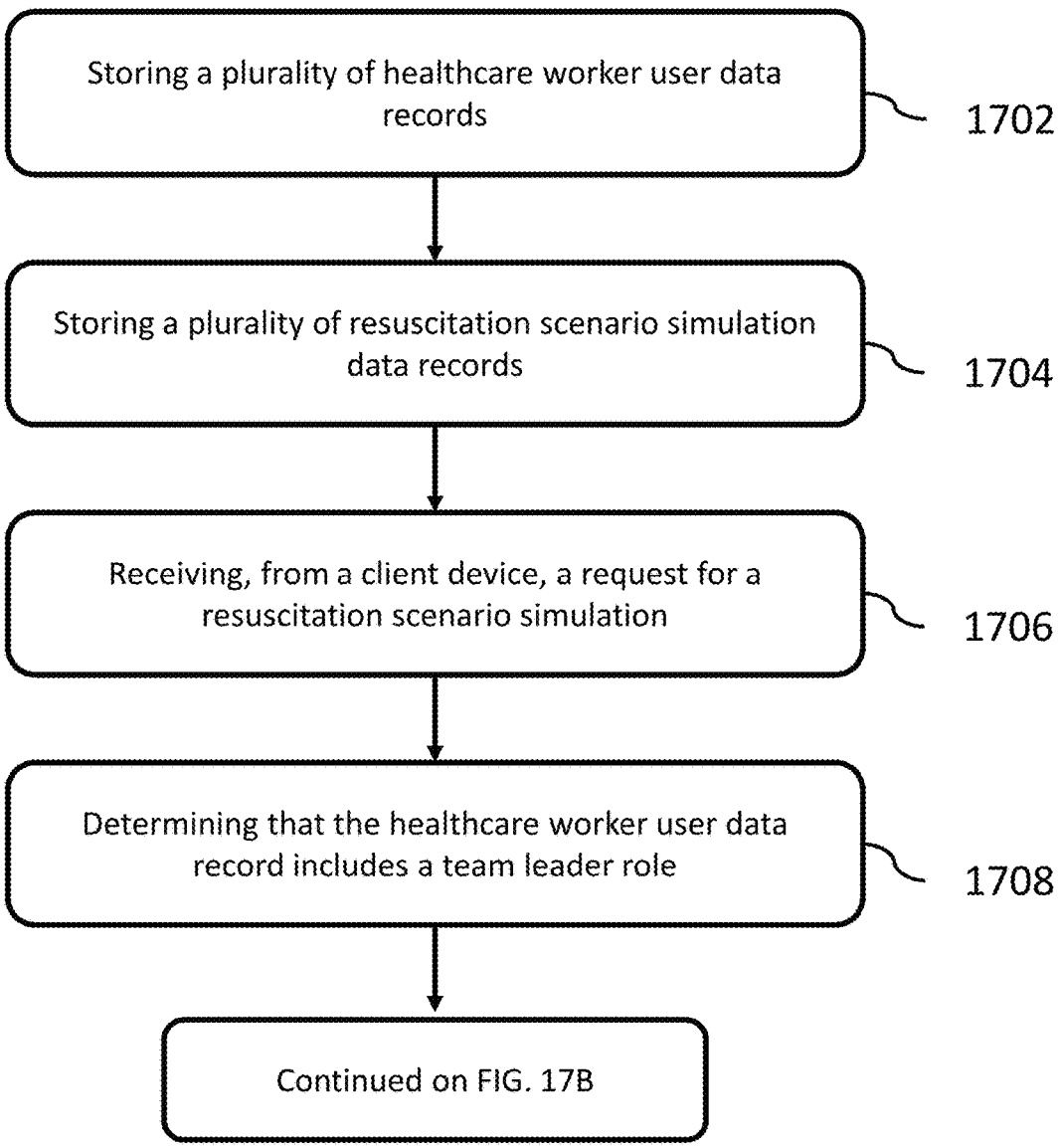
FIG. 17A is a flowchart diagram illustrating another exemplary embodiment of a method for health education, certification, and recordation.

FIGS. 17A-B depict one embodiment of a method 1700. The method 1700 may include a computer-implemented resuscitation education simulation method. The method 1700 may include storing 1702, in one or more non-transitory computer storage devices, a healthcare worker user data record. The method 1700 may include storing 1704, in the one or more non-transitory computer storage devices, a plurality of resuscitation scenario simulation data records. The method 1700 may include receiving 1706, from a client device, a request for a resuscitation scenario simulation. The method 1700 may include determining 1708 that the healthcare worker user data record includes a team leader role. The method 1700 may include generating 1710, at the one or more servers, a customized resuscitation scenario simulation based on the team leader role of the healthcare worker user data record, and at least a portion of the plurality of resuscitation scenario simulation data records. The method 1700 may include transmitting 1712 the customized resuscitation scenario simulation to the client device.

In one embodiment, storing 1702, in the one or more non-transitory computer storage devices, the healthcare worker user data record may be similar to storing 1602, in one or more non-transitory computer storage devices, a plurality of healthcare worker user data records. Storing 1704, in the one or more non-transitory computer storage devices, the plurality of resuscitation scenario simulation data records may be similar to storing 1604, in the one or more non-transitory computer storage devices, a plurality of healthcare scenario simulation data records. Receiving 1706, from the client device, the request for the resuscitation scenario simulation may be similar to receiving 1606, from a client device, a request for a healthcare scenario simulation.

In some embodiments, determining 1708 that the healthcare worker user data record includes a team leader role may be similar to determining 1608, at one or more servers, an identity of a healthcare worker user. For example, the simulation module 1202 may retrieve team leader role data from the request for the resuscitation scenario simulation or may receive the team leader role data from the account module 114.

In one embodiment, generating 1710, at the one or more servers, the customized resuscitation scenario based on the team leader role of the healthcare worker user data record may include including, in the customized resuscitation scenario, a plurality of healthcare interaction options with a virtual team member in the customized resuscitation scenario. In some embodiments, the plurality of healthcare interaction options may include commands to the virtual team member, questions for the virtual team member, or responses from the virtual team member. The virtual team member may include a simulated medical worker 1304(1)-(5), 1404. In some embodiments, the Q&A interface 1308 or the interaction options 1430 may include the plurality of healthcare interaction options.

In some embodiments, generating 1710, at the one or more servers, the customized resuscitation scenario based on the team leader role of the healthcare worker user data record may include including, in the customized resuscitation scenario, a plurality of decisions. The plurality of decisions may be responsive to a selection made by the healthcare worker user via the client device 120. In one embodiment, a decision may be presented to the healthcare worker user via the Q&A interface 1308 or the interaction options 1430. A decision may include which commands to give, which medications to administer, what equipment to use, etc.

As an example of the method 1700, the server 110 may store 1702, in one or more non-transitory computer storage devices of the server 110, a plurality of healthcare worker user data records. The account module 112 may have access to these healthcare worker user data records. The server 110 may also store 1704, in the one or more non-transitory computer storage devices of the server 110, a plurality of healthcare scenario simulation data records. The simulation module 1202 may have access to these healthcare scenario simulation data records.

The client device 120 may include a desktop computer with a VR headset and hand-held controllers. The desktop computer may include a VR application for simulations, and the VR application may be installed on the desktop computer. A healthcare worker user may run the VR application on the desktop computer and put on the VR headset and hand-held controllers. The healthcare worker user may use the VR headset and hand-held controllers to request a healthcare scenario simulation. The VR application may communicate with the server 110 via the data network 130 to send the request to the simulation module 1202. The request may include an identifier that uniquely identifiers the healthcare worker user. The simulation module 1202 may receive 1706 the request for the resuscitation scenario simulation from the desktop computer. The simulation module 1202 may send the identifier found in the request to the account module 112.

The account module 112 may determine the identity of the healthcare worker user based on the identifier. The identifier may include a username or an ID number (e.g., an employee ID number) of the healthcare worker user. The account module 112 may use the identifier to find a matching identifier in an account database. Once the matching user account for the healthcare worker user is found in the account database, the account module 112 may select, from the plurality of healthcare worker user data records in the account database, a first healthcare worker user data record. The first healthcare worker user data record may correspond to the healthcare worker user using the client device 120. The account module 112 may send at least a portion of the first healthcare worker user data record to the simulation module 1202.

The simulation module 1202 may process the at least a portion of the first healthcare worker user data record to determine 1708 that the healthcare worker user data record includes a team leader role. The processing may include the simulation module 1202 determining that the healthcare worker user is an emergency room physician on the resuscitation team of a hospital. In response to making these determinations, the simulation module 1202 may generate 1710 a customized resuscitation scenario simulation. The customized resuscitation scenario simulation may be customized for a resuscitation team leader. For example, the customized resuscitation scenario simulation may include a scenario in an emergency room. The scenario may include a simulated patient 1402 that is experiencing a heart attack. The scenario may include one or more simulated medical workers 1304(1)-(5), 1404 that are on the resuscitation team. The simulated medical workers 1304(1)-(5), 1404 may be configured to receive commands from the healthcare worker user. The simulation module 1202 may include one or more interactive options 1430. The interactive options 1430 may include commands to the simulated medical workers 1304 (1)-(5), 1404 or requests for information from the 1304(1)- (5), 1404. The simulation module 1202 may include resuscitation team leader-related tasks for the healthcare worker user to complete during the simulation such as making observations regarding the simulated patient 1402 or guiding a simulated medical worker 1304(1), 1404 in resuscitating or stabilizing the simulated patient 1402. The tasks may include one or more sub-steps such as ordering a simulated medical worker 1404(2) to perform chest compressions, check vital signs, etc.

The simulation module 1202 may send the files that make up the customized healthcare scenario simulation to the client device 120 via the data network 130. The client device 120 may receive the files. The VR application may use the files to execute the customized healthcare scenario simulation. The simulation may appear on the VR headset as the GUI 1300 or 1400.

Miscellaneous

In some embodiments, a user of the system 100 may include a person that works at healthcare facility but does not access the system 100 himself or herself but has another person (such as hospital support staff) access the system 100 on the user's behalf. For example, a janitor that works at a hospital may not use a client device 120 to interact with the server 110, however a hospital support staff may use a client device 120 to update the janitor's user account information, track the janitor's progress in maintaining certification in a healthcare protocol, or perform other system 100 functionality.

In some embodiments, a module (such as the account module 112, certification module 114, encounter module 116, walkthrough module 118, or other module) storing data may include the module storing the data in an area of a file system of the server 110 that the module controls. In other embodiments, the module storing data may include the module storing data in a database. The database may be a database stored on the server 110 or may include a database on another device.

In some embodiments, one or more modules of the server 110 may send data to an external data repository. The external data repository may include a PSO. Before the server 110 sends the data to the PSO, the server 110 may strip the data of identifying information or other information such that the data complies with healthcare information regulation (e.g., the Health Insurance Portability and Accountability Act (HIPAA)). In some embodiments, the data sent to the PSO may include a healthcare protocol used on a patient in an actual medical episode, the outcome of using the healthcare protocol, or other data. The PSO may use the received data to improve healthcare protocols, training, or other information. The PSO may send updated healthcare protocol data to the server 110.

Computer Hardware and Software

As will be appreciated by one skilled in the art, aspects of the present disclosure may be embodied as an apparatus, system, method, computer program product, or the like.

Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present disclosure may take the form of a computer program product embodied in one or more computer readable medium(s) having program code embodied thereon.

In some embodiments, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of program code may, for instance, comprise one or more physical or logical blocks of computer instructions which may, for instance, be organized as an object, procedure, or function. Nevertheless, the executables of an identified module need not be physically located together but may comprise disparate instructions stored in different locations which, when joined logically together, comprise the module and achieve the stated purpose for the module.

Indeed, a module of program code may be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single data set or may be distributed over different locations including over different storage devices, and may exist, at least partially, merely as electronic signals on a system or network. Where a module or portions of a module are implemented in software, the program code may be stored and/or propagated on in one or more computer readable medium(s).

The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processor devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processor device receives computer readable program instructions from the network and forwards the computer readable program instructions for storage in a computer readable storage medium within the respective computing/processor device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the C programming language or similar programming languages. The computer readable program instructions may execute on a supercomputer, a compute cluster, or the like. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations or block diagrams of methods, apparatuses, systems, or computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The schematic flow chart diagrams included herein are generally set forth as logical flow chart diagrams. As such, the depicted order and labeled steps are indicative of one embodiment of the presented method. Other steps and methods may be conceived that may be equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The schematic flowchart diagrams and/or schematic block diagrams in the Figures illustrate the architecture, functionality, and operation of possible implementations of apparatuses, systems, methods and computer program products according to various embodiments of the present disclosure. In this regard, each block in the schematic flowchart diagrams and/or schematic block diagrams may represent a module, segment, or portion of code, which comprises one or more executable instructions of the program code for implementing the specified logical function(s).

It should also be noted that, in some alternative implementations, the functions noted in the block may occur out of the order noted in the Figures. For example, two blocks shown in succession may, in fact, be executed concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A method for operating a healthcare training mannequin system, comprising:
storing, in a user account database hosted on one or more non-transitory computer storage devices, a plurality of healthcare worker user database records, wherein each of the plurality of healthcare worker user database records includes data indicating a healthcare specialty of a corresponding healthcare worker;
storing, in the one or more non-transitory computer storage devices, a plurality of healthcare scenario simulation data records;
receiving, from a client device in data communication with the one or more non-transitory computer storage devices, a request for a healthcare scenario simulation, wherein the request includes a user identifier configured to uniquely identify a user account in the user account database;
selecting, from the plurality of healthcare worker user databases records, a first healthcare worker user database record based on the user identifier received from the client device;
retrieving, from the selected first healthcare worker user database record, the data indicating the specialty of the corresponding healthcare worker, wherein the specialty includes an emergency room physician specialty;
generating, at one or more servers, a customized healthcare scenario simulation, wherein generating the customized healthcare scenario simulation includes the one or more servers
automatically selecting, based on the emergency room physician specialty retrieved from the first healthcare user database record, a heart attack task from the plurality of healthcare scenario simulation data records, and
constructing the customized healthcare scenario simulation, including the heart attack task;
transmitting, from the one or more servers, the customized healthcare scenario simulation to the client device, wherein
the client device comprises a data-enabled electronic healthcare training mannequin in data communication with the one or more servers, and
the electronic healthcare training mannequin, in response to receiving the heart attack task, is configured to detect a plurality of chest compressions generated via interaction by the healthcare worker; and
transmitting, from the electronic healthcare training mannequin to the one or more servers, interaction data based on the plurality of chest compressions.

2. The method for operating the healthcare training mannequin system of claim 1, wherein each of the plurality of healthcare worker user database record further comprises data indicating at least one of:
a role of the corresponding healthcare worker user; or
a team of the corresponding healthcare worker user.

3. The method for operating the healthcare training mannequin system of claim 2, wherein the data indicating the role of the corresponding healthcare worker user comprises data indicating at least one of:
a nurse;
a medication nurse;
an emergency medical technician; or
a physician.

4. The method for operating the healthcare training mannequin system of claim 1, wherein the first healthcare worker user database record further comprises one or more healthcare assessment results of the healthcare worker user.

5. The method for operating the healthcare training mannequin system of claim 1, where generating, at the one or more servers, the customized healthcare scenario simulation is further based on at least one of:
historical training data;
clinical data;
adaptive training data; or
baseline results.

6. The method for operating the healthcare training mannequin system of claim 1, wherein the client device comprises at least one of:
a mobile computer device; or
a virtual reality headset device.

7. The method for operating the healthcare training mannequin system of claim 1, wherein:
generating, at the one or more servers, the customized healthcare scenario simulation further comprises automatically selecting a plurality of healthcare tasks from the plurality of healthcare scenario simulation data records, wherein each of the second plurality of healthcare tasks includes data indicating a role retrieved from the first healthcare user database record; and
constructing the customized healthcare scenario simulation further comprises including, in the customized healthcare scenario simulation, the plurality of healthcare tasks.

8. The method for operating the healthcare training mannequin system of claim 7, wherein the plurality of healthcare tasks comprises a plurality of actions performable by the healthcare worker user via the client device.

9. The method for operating the healthcare training mannequin system of claim 1, wherein:
generating, at the one or more servers, the customized healthcare scenario simulation further comprises automatically selecting a plurality of healthcare questions from the plurality of healthcare scenario simulation data records; and
constructing the customized healthcare scenario simulation further comprises including, in the customized healthcare scenario simulation, the plurality of healthcare questions.

10. The method for operating the healthcare training mannequin system of claim 1, wherein:
generating, at the one or more servers, the customized healthcare scenario simulation further comprises automatically selecting a healthcare problem from the plurality of healthcare scenario simulation data records; and
constructing the customized healthcare scenario simulation further comprises including, in the customized healthcare scenario simulation, the healthcare problem.

11. The method for operating the healthcare training mannequin system of claim 1, further comprising receiving, from the client device, a result of the customized healthcare scenario simulation at the one or more servers.

12. The method for operating the healthcare training mannequin system of claim 11, further comprising updating a progress of the healthcare worker user in a healthcare protocol certification program based on the result of the customized healthcare scenario simulation.

13. A healthcare training mannequin system, comprising:
one or more non-transitory computer storage devices configured to host a user account database;
at least one computer processor;
a data-enabled electronic healthcare training mannequin in data communication with the at least one computer processor; and
a non-transitory computer-readable storage medium storing computer-readable instructions, wherein the computer-readable instructions, when executed by the at least one computer processor, cause the at least one computer processor to
store, in the user account database of the one or more non-transitory computer storage devices, a plurality of healthcare worker user database records, wherein each of the plurality of healthcare worker user database records includes data indicating a healthcare specialty of a corresponding healthcare worker,
store, in the one or more non-transitory computer storage devices, a plurality of healthcare scenario simulation data records,
receive, from a client device in data communication with the one or more non-transitory computer storage devices, a request for a healthcare scenario simulation, wherein the request includes a user identifier configured to uniquely identify a user account in the user account database,
select, from the plurality of healthcare worker user database records, a first healthcare worker user database record based on the user identifier received from the client device,
retrieve, from the selected first healthcare worker user database record, the data indicating the specialty of the corresponding healthcare worker, wherein the specialty includes an emergency room physician specialty,
generate a customized healthcare scenario simulation, wherein generating the customized healthcare scenario simulation includes the at least one computer processor
automatically selecting, based on the emergency room physician specialty retrieved from the first healthcare user database record, a heart attack task from the plurality of healthcare scenario simulation data records, and
constructing the customized healthcare scenario simulation, including the heart attack task, and
transmit, over a data network, the customized healthcare scenario simulation to the client device,
wherein the electronic healthcare training mannequin, in response to receiving the heart attack task, is configured to
detect a plurality of chest compressions generated via interaction by the healthcare worker, and
transmit, to the at least one processor, interaction data based on the plurality of chest compressions.

14. The healthcare training mannequin system of claim 13, wherein:
generating the customized healthcare scenario simulation further comprises automatically selecting, from the plurality of healthcare scenario simulation data records a plurality of healthcare tasks, wherein each of the plurality of healthcare tasks includes data indicating a role retrieved from the first healthcare user database record,
a plurality of healthcare questions responsive via the client device; and
a healthcare problem exhibited by a virtual patient; and
constructing the customized healthcare scenario simulation further comprises including the plurality of healthcare tasks, the plurality of healthcare questions, and the healthcare problem in the customized healthcare scenario simulation.

15. The healthcare training mannequin system of claim 13, wherein the data indicating the role retrieved from the first healthcare worker user database record comprises data indicating a team leader role.

16. The healthcare training mannequin system of claim 15, wherein:
generating the customized healthcare scenario simulation further comprises automatically selecting, from the plurality of healthcare scenario simulation data records, a plurality of healthcare interaction options with a virtual team member; and
constructing the customized healthcare scenario simulation further comprises including, in the customized healthcare scenario simulation, the plurality of healthcare interaction options with the virtual team member.

17. A computer-implemented resuscitation education simulation method, comprising:
storing, in a user account database hosted on one or more non-transitory computer storage devices, a healthcare worker user database record, wherein each of the plurality of healthcare worker user database records includes data indicating a role of a corresponding healthcare worker;
receiving at one or more servers, from a client device in data communication with the one or more non-transitory computer storage devices, a request for a resuscitation scenario simulation, wherein the request includes a user identifier configured to uniquely identify a user account in the user account database;
selecting, from the plurality of healthcare worker user databases records, a first healthcare worker user database record based on the user identifier received from the client device;
retrieving, from the selected first healthcare worker user database record, the data indicating the role of the corresponding healthcare worker, wherein the role of the first healthcare worker user database record comprises a team leader role;
generating, at the one or more servers, a customized resuscitation scenario simulation, wherein generating the customized resuscitation scenario simulation includes the one or more servers
automatically selecting, based on the team leader role, a plurality of team member commands from the plurality of healthcare scenario simulation data records, wherein each of the plurality of team member commands includes a command from the healthcare worker to a virtual team member, and
constructing the customized resuscitation scenario simulation, including the plurality of team member commands;
transmitting, from the one or more servers, the customized resuscitation scenario simulation to the client device;
receiving a selection of a team member command of the plurality of team member commands from the healthcare worker, wherein the selected team member command comprises a command to the virtual team member to resuscitate a virtual patient; and generating a response for the virtual team member in response to receiving the command to the virtual team member to resuscitate the virtual patient.

18. The computer-implemented resuscitation education simulation method of claim 17, wherein:
wherein the client device comprises a virtual reality (VR) headset wearable by the healthcare worker;
generating, at the one or more servers, the customized resuscitation scenario further includes automatically selecting, based on the team leader role of the first healthcare worker user database record, a plurality of healthcare interaction options with the virtual team member, wherein the plurality of healthcare interaction options and the virtual team member are viewable via the VR headset; and
constructing the customized resuscitation scenario simulation comprises including, in the customized resuscitation scenario, the plurality of healthcare interaction options with the virtual team member.

19. The computer-implemented resuscitation education simulation method of claim 18, wherein the response for the virtual team member comprises:
an audio response produced via the VR headset;
a text response viewable via the VR headset; or
the virtual team member performing chest compressions.

20. The computer-implemented resuscitation education simulation method of claim 17, wherein:
generating, at the one or more servers, the customized resuscitation scenario further includes automatically selecting, based on the team leader role of the healthcare worker user database record, a plurality of decisions, wherein the plurality of decisions are response to a selection made by the first healthcare worker user via the client device; and
constructing the customized resuscitation scenario simulation comprises including, in the customized resuscitation scenario, the plurality of decisions.

* * * * *